US006743968B2

(12) United States Patent
Dellaporta et al.

(10) Patent No.: US 6,743,968 B2
(45) Date of Patent: Jun. 1, 2004

(54) METHODS AND COMPOSITIONS TO REDUCE OR ELIMINATE TRANSMISSION OF A TRANSGENE

(75) Inventors: Stephen L. Dellaporta, Branford, CT (US); Maria A. Moreno, Branford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/794,384

(22) Filed: Feb. 28, 2001

(65) Prior Publication Data

US 2002/0144305 A1 Oct. 3, 2002

Related U.S. Application Data

(60) Provisional application No. 60/185,524, filed on Feb. 28, 2000.

(51) Int. Cl.[7] .......................... A01H 1/02; C12N 15/55; C12N 15/82
(52) U.S. Cl. ..................... 800/274; 800/271; 800/287; 800/303; 800/278; 435/199
(58) Field of Search .............................. 800/271, 274, 800/278, 287, 303, 300, 288, 302, 279; 435/199, 320.1, 419

(56) References Cited

U.S. PATENT DOCUMENTS

| | | | |
|---|---|---|---|
| 5,086,169 A | 2/1992 | Mascarenhas | 536/27 |
| 5,412,085 A | 5/1995 | Allen et al. | 536/24.1 |
| 5,451,513 A | 9/1995 | Maliga et al. | 435/172.3 |
| 5,489,520 A | 2/1996 | Adams et al. | 435/172.3 |
| 5,501,967 A | 3/1996 | Offringa et al. | 435/172.3 |
| 5,527,695 A | 6/1996 | Hodges et al. | 435/172.3 |
| 5,545,545 A | 8/1996 | Gengenbach et al. | 435/172.3 |
| 5,545,546 A | 8/1996 | Allen et al. | 435/172.3 |
| 5,554,798 A | 9/1996 | Lundquist et al. | 800/205 |
| 5,576,203 A | 11/1996 | Hoffman | 435/172.3 |
| 5,597,945 A | 1/1997 | Jaynes et al. | 800/205 |
| 5,633,438 A | 5/1997 | Baszczynski et al. | 800/205 |
| 5,641,664 A | 6/1997 | D'Halluin et al. | 435/172.3 |
| 5,689,042 A | 11/1997 | Amasino et al. | 800/205 |
| 5,736,369 A | 4/1998 | Bowen et al. | 435/172.3 |
| 5,756,324 A | 5/1998 | Baszczynski et al. | 435/172.3 |
| 5,759,538 A | 6/1998 | Donovan et al. | 424/93.461 |
| 5,776,760 A | 7/1998 | Barry et al. | 435/252.3 |
| 6,008,437 A | 12/1999 | Krebbers et al. | 800/303 |
| 6,114,600 A | 9/2000 | Ow et al. | 800/278 |
| 6,147,282 A | 11/2000 | Goff et al. | 800/303 |
| 6,156,953 A | 12/2000 | Preuss et al. | 800/278 |
| 6,172,279 B1 | 1/2001 | Bridges et al. | 800/274 |
| 6,184,439 B1 | 2/2001 | Fabijanski et al. | 800/286 |

FOREIGN PATENT DOCUMENTS

| | | |
|---|---|---|
| WO | 91 02068 A | 2/1991 |
| WO | 93 25695 A | 12/1993 |
| WO | 96 04393 A | 2/1996 |
| WO | 96 26283 A | 8/1996 |
| WO | 97 13401 A | 4/1997 |

OTHER PUBLICATIONS

Denis et al. Plant Physiology 101(4): 1295–1304, 1993.*
Dale et al. Proc. Natl. Acad. Sci. USA 88 (23): 10558–10562, Dec. 1991.*
Reynaerts et al. Scientia Horticlturae 55 (1–3): 125–139, 1993.*
Turgut et al. Plant Molecules Biology 24 (1): 97–104, 1994.*
Ando et al. (2000) *Biochem. Biophys. Res. Comm.* vol. 272, No. 1, p. 125–128.
Balcells and Coupland (1994) *Plant Mol. Biol.* vol. 24, p. 789–798.
Bao et al. (1996) *Transgenic Res.* vol. 5, No. 2, p. 97–103.
Batzer et al. (1991) *Nucleic Acid Res.* vol. 19, No. 18, p. 5081.
Beals and Goldberg (1997) *Plant Cell* vol. 9, No. 9, p. 1527–1545.
Calderon–Urrea and Dellaporta (1999) *Development* vol. 126, No. 3, p. 435–441.
Carpenter et al. (1992) *Plant Cell*. vol. 4, No. 5, p. 557–571.
Chatterjee and Starlinger (1995) *Mol. Gen. Genet.* vol. 249, No. 3, p. 281–288.
Chen et al. (1992) *Genetics* vol. 130, No. 3, p. 665–676.
Cooney et al. (1988) *Science* vol. 241, p. 456–459.
Cranage et al. (1986) *EMBO J.* vol. 5, No. 11, p. 3057–3063.
Custers et al. (1997) *Plant Mol. Biol.* vol. 35, p. 689–699.
DeLong et al. (1993) *Cell* vol. 74, No. 4, p. 757–768.
Feldmann and Marks (1987) *Mol. Gen. Genet.* vol. 208, No. 1/2, p. 1–9.
Galbiati et al. (2000) *Funct. Integr. Genomics* (Germany) vol. 1, No. 1, p. 25–34.
Gielen et al. (1984) *EMBO J.* vol. 3, No. 4, p. 835–846.
Grebenok et al. (1997) *Plant J.* vol. 11, No. 3, p. 573–586.
Hamilton et al. (1992) *Plant Mol. Biol.* vol. 18, p. 211–218.
Haseloff et al. (1999) *Methods Mol. Biol.* vol. 122, p. 241–259.
Hengartner (1999) *Recent Prog. Horm. Res.* vol. 54, p. 213–222.
Hiei et al. (1997) *Plant Mol. Biol.* vol. 35, p. 205–218.
Kardailsky et al. (1999) *Science* vol. 286, No. 5446, p. 1962–1965.
Kay et al. (1997) *Proc. Natl. Acad. Sci. U.S.A.* vol. 94, No. 24, p. 12744–12746.

(List continued on next page.)

*Primary Examiner*—David T. Fox
(74) *Attorney, Agent, or Firm*—Morgan, Lewis & Bockius

(57) ABSTRACT

Genetic constructs and methods are disclosed for the production, maintenance and control of transgenes in transgenic eukaryotic organisms that undergo meiosis in which pollen or sperm can be outcrossed; this includes: transgenic animals, plant cells, plant tissues and whole plants. More specifically, this invention relates to the control of transgene transmission by male and/or female gametes or gametophytes using a gametophytic sterility trait (GST). The genetic constructs and methodologies of the present invention provide the ability to control the undesired spread of transgenes. In addition, this invention also provides the tools and methodologies to enrich a plant or other eukaryotic genome for dispersed and/or stable transposition events.

7 Claims, 5 Drawing Sheets

OTHER PUBLICATIONS

Kim and An (1992) *Transgenic Res.* vol. 1, No. 4, p. 188–194.
Klee et al. (1987) *Mol. Gen. Genet.* vol. 210, No. 3, p. 437–442.
Krysan et al. (1999) *Plant Cell* vol. 11, No. 12, p. 2283–2290.
Kumar et al. (1997) *Leukemia* vol. 11, Supp. 3, p. 385–386.
Lankenau et al. (1994) *Mol. Cell. Biol.* vol. 14, No. 3, p. 1764–1775.
Li and Starlinger (1990) *Proc. Natl. Acad. Sci. U.S.A.* vol. 87, No. 16, p. 6044–6048.
Lee et al. (1988) *EMBO J.* vol. 7, No. 5, p. 1241–1248.
Long et al. (1997) *Plant J.* vol. 11, No. 1, p. 145–148.
Martienssen (1998) *Proc. Natl. Acad. Sci. U.S.A.* vol. 95, No. 5, p. 2021–2026.
Mather (1943) *J. Genet.* vol. 45, p. 215–235.
McCouch (1998) *Proc. Natl. Acad. Sci. U.S.A.* vol. 95, No. 5, p. 1983–1985.
McCouch et al. (1997) *Plant Mol. Biol.* vol. 35, p. 89–99.
Medberry et al. (1995) *Nucl. Acids Res.* vol. 23, No. 3, p. 485–490.
Moon et al. (1999) *Plant Mol. Biol*, vol. 40, p. 167–177.
Moreno et al. (1992) *Genetics* vol. 131, No. 4, p. 939–956.
Murphy and Lagarias (1997) *Curr. Biol.* vol. 7, No. 11, p. 870–876.

Nelson and Krawetz (1995) *DNA Sequence–J. Seq. Mapping* vol. 5, p. 329–337.
Odell et al. (1985) *Nature* vol. 313, No. 6004, p. 810–812.
Ohtsuka et al. (1985) *J. Biol. Chem.* vol. 260, No. 5, p. 2605–2608.
Quaedvlieg et al. (1998) *Plant Mol. Biol.* vol. 37, p. 715–727.
Restrepo–Hartwig and Carrington (1992) *J. Virology* vol. 66, No. 9, p. 5662–5666.
Skarnes (1990) *Biotechnology* vol. 8, p. 827–831.
Sundaresan (1996) *Trends Plant Sci.* vol. 1, No. 6, p. 184–190.
Sundaresan et al. (1995) *Genes Dev.* vol. 9, No. 14, p. 1797–1810.
Takken et al. (1998) *Plant J.* vol. 14, No. 4, p. 401–411.
Thompson et al. (1987) *EMBO J.* vol. 6, No. 9, p. 2519–2523.
Tissier et al. (1999) *Plant Cell .* vol. 11, No. 10, p. 1841–1852.
White et al. (1990) *Nucl. Acids Res.* vol. 18, No. 4, p. 1062.
Yazynin et al. (1999) *FEBS Lett.* vol. 452, No. 3, p. 351–354.

* cited by examiner

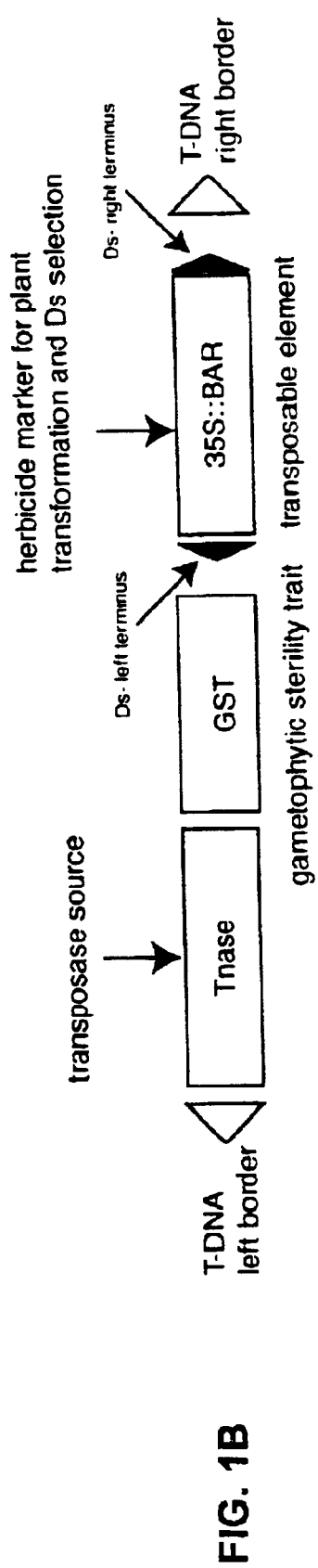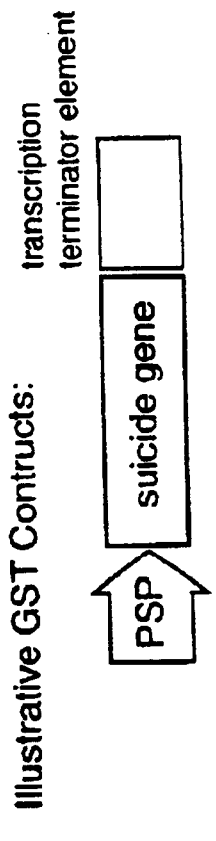

FIG. 2
STRATEGY TO ELIMINATE TRANSGENES AND TO SELECT FOR DISPERSED TRANSPOSITIONS
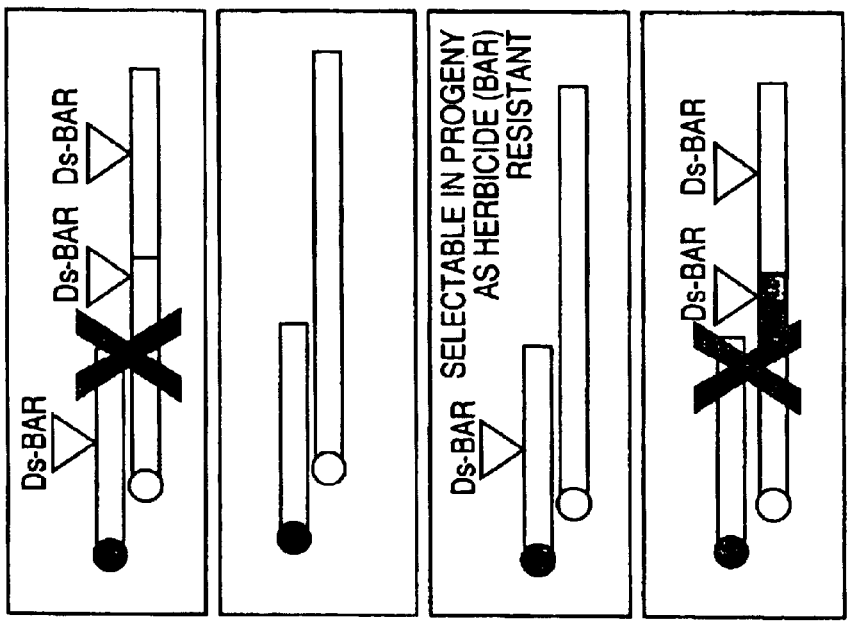
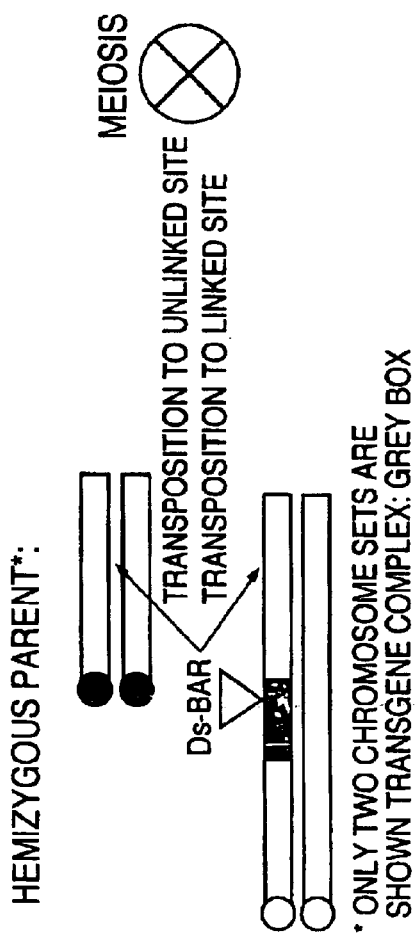

GST CONSTRUCTS pYU846- TRANSPOSASE CONSTRUCT

METHODS AND COMPOSITIONS TO REDUCE OR ELIMINATE TRANSMISSION OF A TRANSGENE

CROSS REFERENCES TO RELATED APPLICATIONS

This application claims priority to Provisional Application 60/185,524, filed Feb. 28, 2000, which is hereby incorporated by reference in its entirety.

STATEMENT OF RIGHTS TO INVENTIONS MADE UNDER FEDERALLY SPONSORED RESEARCH

This invention was partially made with government support under Grant Nos. NIH GM R01 GM38148 and NSF 61-2558.

FIELD OF THE INVENTION

This invention relates generally to the production, maintenance and control of transgenes in transgenic eukaryotic organsims that undergo meiosis in which pollen or sperm can be outcrossed; this includes: transgenic animals, plant cells, plant tissues and whole plants. More specifically, this invention relates to the control of transgene transmission by male and/or female gametes or gametophytes. The genetic constructs and methodologies of the present invention provide the ability to control the undesired spread of transgenes. In addition, this invention also provides the tools and methodologies to enrich a plant genome, or any other eukaryotic genome, for dispersed and/or stable transposition events.

BACKGROUND OF THE INVENTION

All publications and patent applications herein are incorporated by reference to the same extent as if each individual publication or patent application was specifically and individually indicated to be incorporated by reference.

Transgenic crops and the application of biotechnology are dramatically altering seed and agrochemical businesses throughout the world. The seeds of commercially important crops have been genetically engineered to be resistant to herbicides and pests, especially insect pests. According to surveys by the United States Department of Agriculture (June, 2000), genetically modified corn, soybeans and cotton were grown on approximately 25%, 54% and 61%, respectively, of the total U.S. acres for each crop in 2000.

The uncontrolled transmission of heterologous traits in commercially important crop plants is currently a major concern throughout the world and especially within the agricultural community. The undesired dissemination of transgenic pollen may unintentionally harm beneficial insects and may result in the spread of transgenes to related plant species leading to the contamination of food products and the production of herbicide- and pesticide-resistant weedy species.

The biotechnology industry is interested in transferring traits such as tolerances to drought, insects, diseases, salinity, frost and herbicides into cultivated plants which might confer an adaptive advantage over wild plants. Several crop species are known to be cross-compatible with wild species and it is possible that these traits could be inadvertently transferred to wild weedy relatives through sexual hybridization leading to possible economic and ecological harm. Since most forage and turf grasses have undergone relatively little domestication and may even be considered weeds in certain instances (e.g., bermudagrass), there is a high probability of greater problems in the ultimate release and use of such genetically transformed plants. Because forage grasses, in general, are not highly domesticated, possess weedy characteristics, and are highly outcrossing, special difficulties may be encountered in the ultimate release of transgenic forage grasses.

It would be highly desirable to have a method to prevent the undesired transmission of heterologous traits in commercially important crop plants. If this could be achieved, genetic leakage of heterologous traits would be brought under control and the spread of these traits to undesired recipients would be curtailed. Thus, the need exits for a genetic system that selects against male or female gametophytes containing transgenes, thereby preventing, eliminating or reducing the undesired transmission of heterologous traits. In particular, there is a need for a genetic system which allows for the transmission of non-transgenic (i.e., wild type) gametophytes while preventing the transmission of the transgenic (i.e., heterologous) gametophytes from the same plant.

Thus, an object of this invention is to provide recombinant nucleic acid constructs and methods for controlling, reducing or eliminating the undesired transmission of heterologous traits in commercially important crop plants.

SUMMARY OF THE INVENTION

The instant invention is directed to genetic constructs and methods for controlling the spread of heterologous traits in plants. Control is achieved by providing a sex-specific promoter operably linked to a suicide gene that selects against male or female gametes containing the suicide gene. The suicide gene locus is termed the "gametophytic suicide trait" (GST) (FIG. 1A). By linking a transgene of interest to a suicide gene under the control of a sex-specific promoter, transmission of the transgene to progeny is effectively eliminated, reduced or prevented because no gametes bearing the GST will be produced.

In one aspect, the invention can be said to broadly consist of a suicide gene under the control of a pollen-specific promoter linked to a transgene of interest. The transgene complex can be introduced into a virgin plant genome and plants can be selected which are hemizygous for the transgene complex. The only pollen produced by the hemizygous plant will lack the transgene complex due to its physical linkage to the suicide gene. Uncontrolled spread of the heterologous trait encoded by the transgene complex is thereby prevented because no pollen containing the transgene complex is produced.

A second aspect of the invention is based on placing the GST in close proximity to a transposon to produce selective enrichment of dispersed transposition events in progeny cells since only those gametes lacking the GST locus will be viable. Since a fraction of the progeny cells produced from viable gametes will have undergone transposition events, selective enrichment of dispersed transposition events is achieved because the transposon is necessarily no longer linked to the GST (the GST destroys those gametes that inherit the GST gene locus) (FIG. 1B).

Thus, the present invention provides genetic systems which can be used for the elimination of a GST transgene complex and for the selection for unlinked transpositions. By using the GST together with any transgene, one can completely eliminate male (or female in the case of a female gametophytic-specific promoter:suicide construct) transmission of both the GST and the associated transgene (FIG. 2).

This invention provides nucleic acid constructs comprising a male gamete- or female gamete-specific promoter operably linked to a suicide gene, wherein said promoter and said suicide gene combination is linked to a gene of interest.

This invention provides nucleic acid constructs comprising a male gamete- or female gamete-specific promoter operably linked to a suicide gene, wherein the promoter and the suicide gene combination is linked to a gene of interest. This invention further provides such nucleic acid constructs wherein the promoter is selected from the group consisting of a pollen-specific promoter and an ovule-specific promoter. This invention still further provides such nucleic acid constructs wherein the suicide gene is selected from the group consisting of barnase, tasselseed2 and diphtheria toxin A gene. This invention also provides such nucleic acid constructs wherein the gene of interest is selected from the group consisting of a nucleic acid encoding herbicide resistance, antibiotic resistance, insecticide resistance, nitrogen fixation, improved nutrition and cellulose content.

This invention provides nucleic acid constructs comprising a pollen-specific promoter or an ovule-specific promoter operably linked to a suicide gene selected from the group consisting of barnase, tasselseed2 and diphtheria toxin A gene; wherein the promoter and the suicide gene combination is linked to a gene of interest selected from the group consisting of a gene coding for herbicide resistance, antibiotic resistance, insecticide resistance, nitrogen fixation, improved nutrition and cellulose content or other agronomic trait of interest.

This invention provides methods for reducing or eliminating male transmission of a transgene locus in a plant comprising:
  a) transforming a plant cell with a nucleic acid construct in which a male gamete-specific promoter is operably linked to a suicide gene, wherein said promoter and said suicide gene combination is linked to a heterologous polynucleotide;
  b) propagating said transformed plant cell through meiosis to produce male gametes lacking said transgene locus.

This invention also provides methods for reducing or eliminating male transmission of a transgene locus in a plant comprising:
  a) transforming a plant cell with a nucleic acid construct in which a pollen-specific promoter is operably linked to a suicide gene;
    i) wherein said suicide gene is selected from the group consisting of barnase, tasselseed2 and diphtheria toxin A gene;
    ii) wherein said promoter and said suicide gene combination is linked to a heterologous polynucleotide;
    iii) wherein said heterologous polynucleotide is selected from the group consisting of DNA encoding herbicide resistance, antibiotic resistance, insecticide resistance, nitrogen fixation, improved nutrition and cellulose content;
  b) propagating said transformed plant cell through meiosis to produce male gametes lacking said transgene locus.

This invention also provides methods for reducing or eliminating female transmission of a transgene locus in a plant comprising:
  a) transforming a plant cell with a nucleic acid construct in which a female gamete-specific promoter is operably linked to a suicide gene, wherein said promoter and said suicide gene combination is linked to a heterologous polynucleotide;
  b) propagating said transformed plant cell through meiosis to produce female gametes lacking said transgene locus.

This invention further provides methods for reducing or eliminating female transmission of a transgene locus in a plant comprising:
  a) transforming a plant cell with a nucleic acid construct in which an ovule-specific promoter is operably linked to a suicide gene;
    i) wherein said suicide gene is selected from the group consisting of barnase, tasselseed2 and diphtheria toxin A gene;
    ii) wherein said promoter and said suicide gene combination is linked to a heterologous polynucleotide;
    iii) wherein said heterologous polynucleotide is selected from the group consisting of DNA encoding herbicide resistance, antibiotic resistance, insecticide resistance, nitrogen fixation, improved nutrition and cellulose content.
  b) propagating said transformed plant cell through meiosis to produce female gametes lacking said transgene locus.

This invention also provides transformed plant cells produced by the methods of the present invention wherein the transformed plant cells are hemizygotic for the nucleic acid construct.

This invention provides nucleic acid constructs comprising a male gamete- or female gamete-specific promoter operably linked to a suicide gene wherein said promoter and said suicide gene combination is linked to a transposable element. This invention also provides such nucleic acid constructs which further comprise one or more transposase genes. This invention further provides such nucleic acid constructs which further comprise one or more genes of interest. This invention still further provides such nucleic acid constructs wherein the gene of interest is associated with the transposable element.

This invention provides nucleic acid constructs in which a pollen-specific promoter or an ovule-specific promoter is operably linked to a suicide gene selected from the group consisting of barnase, tasselseed2 and diphtheria toxin A gene; wherein said promoter and said suicide gene combination is linked to a transposon, wherein said transposon comprises a selectable marker selected from the group consisting of a gene coding for herbicide resistance, antibiotic resistance, insecticide resistance, nitrogen fixation, improved nutrition and cellulose content. This invention also provides such nucleic acid constructs wherein the promoter is selected from the group consisting of a pollen-specific promoter and an ovule-specific promoter. This invention also provides such nucleic acid constructs wherein the suicide gene is selected from the group consisting of barnase, tasselseed2 and diphtheria toxin A gene.

The present invention provides methods for enriching dispersed transposition events in a population of plant cell progeny comprising:
  a) transforming a plant cell with the nucleic acid construct of any one of the aforementioned nucleic acid constructs to produce a transformed plant cell;
  b) propagating said transformed plant cell through meiosis to produce plant cell progeny in which dispersed transposition events are enriched.

The present invention also provides such methods which include the additional step of isolating the plant cell progeny in which dispersed transposition events are enriched. The present invention also provides plant cells and plants which contain dispersed transposition events and, particularly, the plant cells and plants are hemizygotic for the nucleic acid.

The present invention provides nucleic acid constructs comprising a first promoter wherein the first promoter is a male gamete- or female gamete-specific promoter operably linked to a suicide gene and further comprising a nucleic acid encoding a transposase and a nucleic acid encoding a transposon. The present invention also provides such nucleic acid constructs wherein the transposon comprises a second promoter operably linked to a selectable marker, wherein the selectable marker is not a suicide gene.

The present invention provides nucleic acid constructs in which a pollen-specific promoter or an ovule-specific promoter is operably linked to a suicide gene selected from the group consisting of barnase, tasselseed2 and diphtheria toxin A gene, wherein said promoter and said suicide gene combination is linked to a nucleic acid encoding transposase; wherein said promoter and said suicide gene combination linked to said nucleic acid encoding transposase comprise a transgene locus which further comprises a transposon; wherein said transposon comprises a polynucleotide sequence encoding a member selected from the group consisting of herbicide resistance, antibiotic resistance, insecticide resistance, nitrogen fixation, improved nutrition and cellulose content. The present invention provides such nucleic acid constructs wherein the promoter is selected from the group consisting of a pollen-specific promoter and an ovule-specific promoter. The present invention further provides such nucleic acid constructs wherein the suicide gene is selected from the group consisting of barnase, tasselseed2 and diphtheria toxin A gene. The present invention also provides such nucleic acid constructs wherein the transposon comprises a polynucleotide sequence encoding a member selected from the group consisting of herbicide resistance, antibiotic resistance, insecticide resistance, nitrogen fixation, improved nutrition and cellulose content.

The present invention also provides methods for enriching stably dispersed transposition events in a population of plant cell progeny comprising:

a) transforming a plant cell with a nucleic acid constructs of the present invention to produce a transformed plant cell;

b) propagating said transformed plant cell through meiosis to produce plant cell progeny in which stably dispersed transposition events are enriched.

The present invention also provide such methods further comprising the step of isolating the plant cell progeny in which the stably dispersed transposition events are enriched. The invention further provides plant cells isolated by such methods and plants produced from the plant cells.

This invention provides vectors comprising the nucleic acid constructs of the present invention as well as host cells, recombinant plant cells and transgenic plants comprising the vectors of the present invention. More particularly, this invention provides such cells and transgenic plants which are hemizygotic for the nucleic acid constructs.

Other objects, advantages and features of the present invention become apparent to one skilled in the art upon reviewing the specification and the drawings provided herein.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

In the drawings:

FIG. 1A shows an illustrative GST (Gametophytic Sterility Trait) Construct in which a pollen-specific promoter is operably linked to a suicide gene. The GST construct can be physically linked to a gene of interest to form a transgene complex. The GST construct is used to prevent or eliminate transmission of the gene of interest.

FIG. 1B shows an illustrative GST construct linked to a transposable element and a transposase source. This construct can be used to enrich a population of plant cell progeny for stably dispersed transposons.

FIG. 2 shows a generalized strategy for eliminating a transgene complex from meiotic products and to select for dispersed transpositions.

DETAILED DESCRIPTION

Figure 3A:
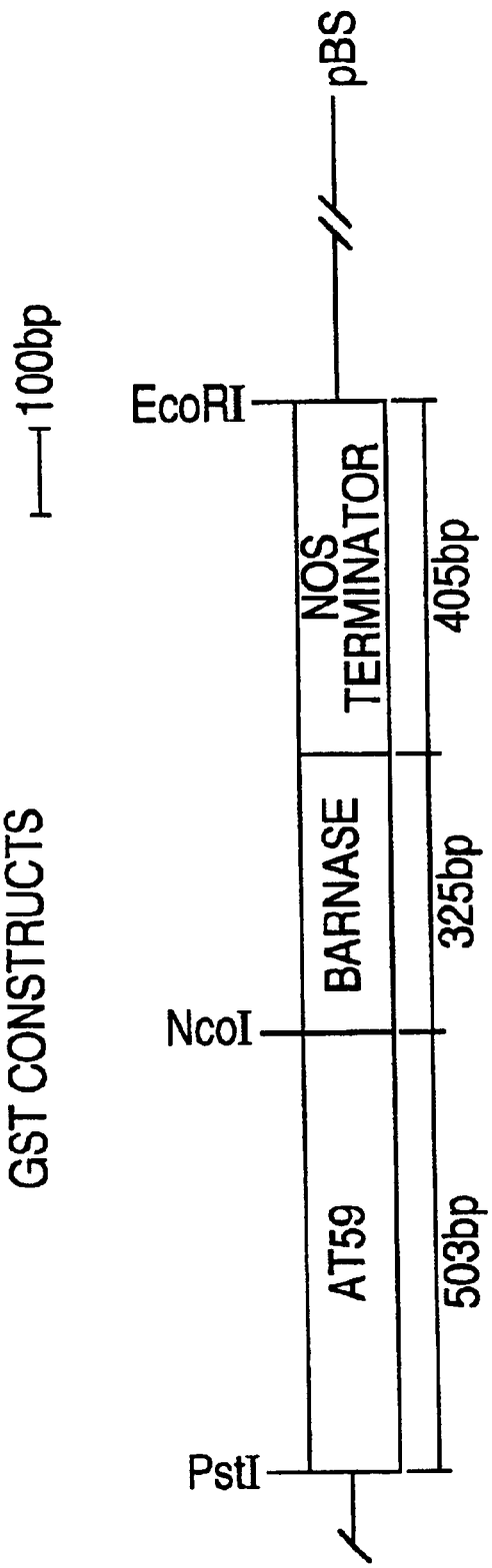
FIGS. 3A and 3B show schematics of GST constructs.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

It will be appreciated from the above that the tools and methods of the present invention have application to all plants that produce gametes. Such plants include, but are not limited to, forage grasses, turf grasses, forage legumes, vegetables, field crops, trees and ornamental flowers.

Definitions

As used herein, the term "allele" refers to any of several alternative forms of a gene.

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food additives, smoking products, pulp production and wood production.

As used herein, the term "cross pollination" or "crossbreeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

The term "dispersed transposition event" refers to the movement of a transposon such that it is no longer linked (i.e. in close proximity) to the transposon launch site (donor site).

The term "female" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "$F_1$"), while that resulting from crossing of F1 individuals is the second filial generation (designated as "F2" or "$F_2$").

The term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

The term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, plant, or group of plants.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

A "heterologous polynucleotide" or a "heterologous nucleic acid" or an "exogenous DNA segment" refers to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

A "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

The term "male" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to emasculation (e.g., by removing the ovary).

As used herein, the term "mass selection" refers to a form of selection in which individual plants are selected and the next generation propagated from the aggregate of their seeds.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605–2608; Cassol et al. (1992); Rossolini et al. (1994) Mol. Cell. Probes 8:91–98). The term nucleic acid is used interchangeably with gene, cDNA, and mRNA encoded by a gene.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the term "ovule" refers to the female gametophyte, whereas the term "pollen" means the male gametophyte.

As used herein, the term "ovule-specific promoter" refers broadly to a nucleic acid sequence that regulates the expression of nucleic acid sequences selectively in the cells or tissues of a plant essential to ovule formation and/or function and/or limits the expression of a nucleic acid sequence to the period of ovule formation in a plant.

As used herein, the term "pollen-specific promoter" refers broadly to a nucleic acid sequence that regulates the expression of nucleic acid sequences selectively in the cells or tissues of a plant essential to pollen formation and/or function and/or limits the expression of a nucleic acid sequence to the period of pollen formation in the plant.

As used herein, the term "phenotype" refers to the observable characters of an individual cell, cell culture, plant, or group of plants which results from the interaction between that individual's genetic makeup (i.e., genotype) and the environment.

As used herein, the term "plant" refers to whole plants, plant organs (e.g., leaves, stems, roots, etc.), seeds and plant cells and progeny of it. The class of plants that can be used in the methods of the invention is generally as broad as the class of higher plants amenable to transformation techniques, including both monocotyledonous and dicotyledonous plants.

As used herein, the term "promoter" refers to a region of DNA involved in binding RNA polymerase to initiate transcription.

As used herein, the term "recombinant" refers to a cell, tissue or organism that has undergone transformation with recombinant DNA. The original recombinant is designated as "R0" or "$R_0$." Selfing the R0 produces a first transformed generation designated as "R1" or "$R_1$."

As used herein, the term "self-incompatible" means the failure, following mating or pollination, of a male gamete and a female gamete to achieve fertilization, where each of them is capable of uniting with other gametes of the breeding group after similar mating or pollination (Mather, *J. Genet.* 25:215–235 (1943)).

As used herein, the term "self pollinated" or "self-pollination" means the pollen of one flower on one plant is applied (artificially or naturally) to the ovule (stigma) of the same or a different flower on the same plant.

As used herein, the term "stably dispersed transposition event" refers to a dispersed transposition that does not undergo further transpositions such as secondary transposition events.

As used herein, the term "suicide gene" refers to any gene that expresses a product that is fatal to the cell expressing the suicide gene.

As used herein, the term "synthetic" refers to a set of progenies derived by intercrossing a specific set of clones or seed-propagated lines. A synthetic may contain mixtures of seed resulting from cross-, self-, and sib-fertilization.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms, plants, and progeny of plants which have received a foreign or modified gene by one of the various methods of transformation, wherein the foreign or modified gene is from the same or different species than the species of the plant, or organism, receiving the foreign or modified gene.

As used herein, the term "transposase" refers to an enzyme, enzymes, or more generally, a molecule or molecules that catalyze a transposition event.

As used herein, the term "tansposition event" refers to the movement of a transposon from a donor site to a target site.

As used herein, the term "transposon" refers to a genetic element, including but not limited to segments of DNA or RNA that can move from one chromosomal site to another.

As used herein, the term "variety" refers to a subdivision of a species, consisting of a group of individuals within the species that are distinct in form or function from other similar arrays of individuals.

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Overview of the Invention

Constructs and methods are described for the destruction of the male or female gametophyte (microspores or megaspores) for the purposes of eliminating transmission of a transgene locus (gene of interest). In one embodiment, microspore destruction is genetically engineered using a pollen-specific promoter fused to an appropriate suicide gene or through the use of genetic mutations that are unable to be transmitted through one of the sexes.

When hemizygous, eliminating transmission of a transgene locus is achieved by linking a gene of interest to a suicide gene under the control of a male or female-specific promoter. This construct, termed the "gametophytic suicide trait" (GST) induces cell death that is restricted to microspores or megaspores, thereby effectively reducing or eliminating transmission of the gene of interest that is linked to the GST. Since the GST/transgene construct is hemizygous, 50% of the pollen grains will be viable and non-transgenic. Thus, the transmission of a transgene can be controlled while permitting pollination to occur so as to achieve fertilization and ultimately obtain a seed supply for planting or food use. Since many plants produce an overabundance of pollen, the loss of 50% of the pollen produced will not adversely affect seed set for most plant species. As one example, corn (*Zea mays*) produces as many as $10^7$ pollen grains/day for a plant in the peak of a 7 day flowering period (Coe et al., The Genetics of Corn, In: Corn and Corn Improvement. Third Edition. Editors: Sprague et al., (1988) pp. 81–258).

Eliminating male transmission of a transgene locus can also be used as a novel strategy to enrich for dispersed and/or stable transposition events. This is accomplished by engineering a "transgene complex" containing a transposable element and/or transposase gene along with a "gametophytic suicide trait" (GST). The GST induces cell death that is restricted to microspores, severely reducing male transmission of nearby chromosomal regions and other transgenes, including the transposon (donor element) and/or transposase gene within the transgene complex.

When the transgene complex is heterozygous in the male parent, approximately 50% of the microspores will undergo destruction, thereby preventing male transmission of the transgene complex and greatly reducing male transmission of linked transposed elements. This elimination of the transposon donor site and nearby transpositions has the net effect of enriching for pollen containing unlinked transpositions and transposed elements that have recombined with the donor transgene complex.

Surviving transposition events can be readily selected in offspring by including an herbicide selectable marker gene within the transposable element. The GST can also be physically linked to the transposase source to eliminate gametes containing a source of transposase. This arrangement prevents transmission of the transposase source to gametes, thereby stabilizing insertions in subsequent generations.

All three components—the suicide gene or mutation, the transposase source and the transposon—can be engineered as a unit to provide a robust method of generating dispersed, stable transpositions. An alternative strategy to microspore destruction is to engineer ovule semi-sterility using a megaspore suicide trait to eliminate female transmission of the transgene complex.

I. Nucleic Acids

A. Promoters

There are many excellent examples of suitable promoters to drive pollen-specific expression in plants. Pollen-specific promoters have been identified in many plant species such as maize, rice, tomato, tobacco, Arabidopsis, Brassica, and others (Odell, T. O., et al. (1985) Nature 313:810–812; Marrs, K. A., et al, (1993) Dev Genet, Vol. 14/1:27–41; Kim, (1992) Transgenic Res, Vol. 1/4:188–94; Carpenter, J. L., et al. (1992) Plant Cell Vol. 4/5:557–71; Albani, D. et al., (1992) Plant J. 2/3:331–42; Rommens, C. M., et al. (1992), Mol. Gen. Genet., Vol. 231/3:433–41; Kloeckener-Gruissem, et al., (1992) Embo J, Vol. 11/1:157–66; Hamilton, D. A. et al., (1992), Plant Mol Biol, Vol. 18/2:211–18; Kyozuka, J., et al. (1991), Mol. Gen. Genet., Vol. 228/1–2:40–8; Albani, D. et. al (1991) Plant Mol Biol Vol. 16/4:501–13; Twell, D. et al. (1991) Genes Dev. 5/3:496–507; Thorsness, M. K. et al., (1991) Dev. Biol Vol. 143/1:173–84; McCormick, S. et al. (1991) Symp Soc Exp Biol Vol. 45:229–44; Guerrero, F. D. et al. (1990) Mol Gen Genet Vol 224/2:161–8; Twell, D. et al., (1990) Development Vol. 109/3:705–13; Bichler, J. et al. (1990), Eur J Biochem Vol. 190/2:415–26; van Tunen, et al. (1990), Plant Cell Vol 2/5:393–401; Siebertz, B. et al., (1989) Plant Cell Vol 1/10:961–8; Sullivan, T. D. et al, (1989) Dev Genet Vol 10/6:412–24; Chen, J. et al. (1987), Genetics Vol 116/3:469–77). Several other examples of pollen-specific promoters can be found-in GenBank. Additional promoters are also provided in U.S. Pat. Nos. 5,086,169; 5,756,324; 5,633,438; 5,412,085; 5,545,546 and 6,172,279.

There are also several other eukaryotic sex-specific promoters suitable for use in the instant invention. Examples include: the mouse spermatocyte-specific Pgk-2 promoter (Ando et al. (2000) Biochem. Biophys. Res. Comm. 272/1:125–8); the PACAP testis-specific promoter (Daniel et al. (2000) Endocrinology, 141/3:1218–27); the mouse mSP-10 spermatid-specific promoter (Reddi et al. (1999) Biology of Reproduction, 61/5:1256–66); the mouse sperm-specific promoter (Ramara et al. (1998) J. Clin. Invest. 102/2:371–8); the mouse and rat Hlt promoters (vanWert et al. (1996) J. Cell. Biochem. 60/3:348–62); the human PRM1, PRM2 and TNP2 spermatid-specific promoters (Nelson et al. (1995) DNA Sequence 5/6:329–37); the Drosophila exu sex-specific promoter (Crowley et al (1995) Molec. Gen. Genet. 248/3:370–4); the mouse testis ACE promoter (Zhou et al. (1995) Dev. Genet. 16/2:201–9); the rat GHRH spermatogenic-specific promoter (Srivastava et al. (1995) Endocrinology 136/4:1502–8); the Drosophila testis-specific promoter (Lankenau et al. (1994) Mol. Cell. Biol. 14/3:1764–75); the spermatocyte-specific hst70 gene promoter (Widlak et al. (1994) Acta Biochim. Polonica 41/2:103–5); and the mouse Prm-1 spermatid-specific promoter (Zambrowicz et al. (1993) Proc. Nat'l. Acad. Sci. USA 90/11:5071–5).

For the present invention, any promoter will be suitable if the promoter is specific to one sex (male or female) and specifically drives gene expression after meiosis I when homologous chromosomes have separated into different cells. For instance, gene expression in the tetrad stage of meiosis II, the post-mitotic division of the microspore leading to pollen maturation, the mature pollen grain, or in the germinating pollen grain, would be suitable for the current invention.

B. Suicide Genes

One aspect of the gametophytic suicide trait (GST) is the directed expression of a suicide gene to kill unwanted meiotic products. Examples of genes whose expression results in cell death include, but are not limited to, those that have been described in the literature including the barnase (Custers, J. B., et al., (1997) Plant Mol Biol Vol. 35/6:689–99; Yazynin, S., et al., (1999) FEBS Lett Vol. 452/3:351–4; Goldman, M. H, et al., (1994) Embo J Vol. 13/13:2976–84, 1994), tasselseed2 (DeLong, A, et al., (1993) Cell Vol. 74/4:757–768), and the diptheria toxin A gene (Day, C. D., et al., (1995) Development Vol. 121/9:2887–95). Because suicide gene expression is confined to post-meiosis I, only 50% of the gametes will be eliminated when the transgene is hemizygous and segregates normally in meiosis. Viable gametes will not have inherited the suicide gene.

According to another aspect of the invention, semi-sterility can also be achieved using antisense RNA technology to inhibit expression of a gene, or genes, essential for viability of the pollen or egg. This technology is discussed in more detail below.

Alternatively, mutations that are incapable of transmission through one of the sexes, such as deletions that are not pollen transmitted, can also be used to achieve semi-sterility.

Specific examples of suicide genes include, but are not limited to, the following:

Tasselseed2 (ts2). Genetic and molecular evidence shows that ts2 is required for pistil elimination in both tassel and ear spikelets. ts2 expression in pistil cells is coincident with loss of nuclear integrity and cell death. It is not clear how the ts2 gene product functions in a cell death pathway. On the basis of its similarity to short-chain alcohol dehydrogenases, especially to hydroxysteroid dehydrogenases, two possibilities are theorized. The ts2 product may metabolize a substrate, perhaps a steroid, required for cell viability. Alternatively, TS2 action may result in the formation of a signaling molecule that activates a cell death response. (Calderon-Urrea et al. (1999) Development, 126:435).

Diphtheria Toxin A-chain (DTA). Diphtheria Toxin A-chain (DTA) inhibits protein synthesis, Greenfield et al., Proc. Natl. Acad., Sci.:USA, 80:6853 (1983); Palmiter et al., Cell, 50:435 (1987).

Pectate lyase pelE. Pectate lyase pelE from Erwinia chrysanthemi EC16 degrades pectin, causing cell lysis. Keen et al., J. Bacteriology, 168:595 (1986).

T-urf13 (TURF-13). T-urf13 (TURF-13) from cms-T maize mitochondrial genomes; this gene encodes a polypeptide designated URF13 which disrupts mitochondrial or plasma membranes. Braun et al., Plant Cell, 2:153 (1990); Dewey et al., Proc. Natl. Acad. Sci.:USA, 84:5374 (1987); Dewey et al., Cell, 44:439 (1986).

Gin recombinase. Gin recombinase from phage Mu a gene encodes a site-specific DNA recombinase which will cause genome rearrangements and loss of cell viability when expressed in cells of plants. Maeser et al., Mol. Gen. Genet., 230:170–176 (1991).

Indole acetic acid-lysine synthetase (iaaL). Indole acetic acid-lysine synthetase (iaaL) from *Pseudomonas syringae* encodes an enzyme that conjugates lysine to indoleacetic acid (IAA). When expressed in the cells of plants, it causes altered developments due to the removal of IAA from the cell via conjugation. Romano et al., Genes and Development, 5:438–446 (1991); Spena et al., Mol. Gen; Genet., 227:205–212 (1991); Roberto et al., Proc. Natl. Acad. Sci.:USA, 87:5795–5801.

Barnase. Ribonuclease from *Bacillus amyloliquefaciens*, also known as barnase, digests mRNA in those cells in which it is expressed, leading to cell death. Mariani et al., Nature 347:737–741 (1990); Mariani et al., Nature 357:384–387 (1992).

CytA toxin gene. CytA toxin gene from *Bacillus thuringiensis israeliensis* encodes a protein that is mosquitocidal and hemolytic. When expressed in plant cells, it causes death of the cell due to disruption of the cell membrane. McLean et al., J. Bacteriology, 169:1017–1023 (1987); Ellar et al., U.S. Pat. No. 4,918,006 (1990).

Suitable cell death genes for use as suicide genes in other eukaryotic organisms include: human PDCD9 (programmed cell death 9) and the *Gallus gallus* pro-apoptotic protein p52 (Carim et al. (1999) Cytogenetics and Cell Genetics (Switzerland) 87/1–2:85–8); the *C. elegans* programmed cell death genes CED-3 and EGL-1 (Hengartner et al. (1999) 54:213–22); the gene encoding the mammalian homolog of *C. elegans* CED-3: ICE (interleukin-1 beta-converting enzyme) (Kondo et al. (1998) Investigative Ophthalmology & Visual Science 39/13:2769–74); the genes encoding ICE-like proteases Ich-1L, CPP32beta, Mch2alpha and Mch3alpha (Kondo et al. (1998) 58/5:962–7); or the mammalian cell death gene Nedd2 (Kumar et al. (1997) Leukemia 11 Suppl 3:385–6).

C. Transgenes and Heterologous Nucleic Acids

Genes successfully introduced into plants using recombinant DNA methodologies include, but are not limited to, those coding for the following traits:seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554,798; Powell et al., Science 232:738–743 (1986); Kaniewski et al., Bio/Tech. 8:750–754 (1990); Day et al., Proc. Natl. Acad. Sci. USA 88:6721–6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597,946; Hilder et al., Nature 330:160–163; Johnson et al., Proc. Natl. Acad. Sci. USA, 86:9871–9875 (1989); Perlak et al., *Bio/Tech.* 8:939–943 (1990)); lectins (U.S. Pat. No. 5,276,269); and flower color (Meyer et al., Nature 330:677–678 (1987); Napoli et al., Plant Cell 2:279–289 (1990); van der Krol et al., Plant Cell 2:291–299 (1990)).

Of particular interest are genes that confer resistance to a herbicide. Examples include, but are not limited to, the following:

(i) An herbicide that inhibits the growing point or meristem, such as an imidazalinone or a sulfonylurea. Exemplary genes in this category code for mutant ALS and AHAS enzymes as described, for example, by Lee et al., EMBO J. 7: 1241 (1988), and Miki et al., Theor. Appl. Genet. 80: 449 (1990), respectively.

(ii) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L--phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., Theor. Appl. Genet. 83: 435 (1992). The expression of a Streptomyces bar gene encoding a phosphinothricin acetyl transferase in maize plants results in tolerance to the herbicide phosphinothricin or glufosinate (U.S. Pat. No. 5,489,520, incorporated herein by reference).

For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631 (1990)), the hph gene which confers resistance to the antibiotic hygromycin (Blochinger & Diggelmann, Mol Cell Biol 4: 2929–2931), and the dhfr gene, which confers resistance to methotrexate (Bourouis et al., EMBO J. 2(7): 1099–1104 (1983)).

Transgenic alfalfa plants have been produced using a number of different genes isolated from both alfalfa and non-alfalfa species including, but not limited to, the following: the promoter of an early nodulin gene fused to the reporter gene gusA (Bauer et al., The Plant Journal 10(1):91–105 (1996); the early nodulin gene (Charon et al., Proc. Natl. Acad. of Sci. USA 94(16):8901–8906 (1997); Bauer et al., Molecular Plant-Microbe Interactions 10(1):39–49 (1997)); NADH-dependent glutamate synthase (Gantt, The Plant Journal 8(3):345–358 (1995)); promoter-gusA fusions for each of three lectin genes (Bauchrowitz et al., The Plant Journal 9(1):31–43 (1996)); the luciferase enzyme of the marine soft coral *Renilla reniforms* fused to the CaMV promoter (Mayerhofer et al., The Plant Journal 7(6):1031–1038 (1995)); Mn-superoxide dismutase cDNA (McKersie et al., Plant Physiology 111(4):1177–1181 (1996)); synthetic cryIC genes encoding a *Bacillus thuringiensis* delta-endotoxin (Strizhov et al., Proc. Natl. Acad. Sci. USA 93(26):15012–15017 (1996)); glucanse (Dixon et al., Gene 179(1):61–71 (1996); Masoud et al., Transgenic Research 5(5):313–323)); and leaf senescce gene (U.S. Pat. No. 5,689,042).

Genes successfully transferred into clover using recombinant DNA technologies include, but are not limited to, the following: Bt genes (Voisey et al., supra); neomycin phosphotransferase II (Quesbenberry et al., supra); the pea lectin gene (Diaz et al., Plant Physiology 109(4):1167–1177 (1995); Eijsden et al., Plant Molecular Biology 29(3):431–439 (1995)); the auxin-responsive promoter GH3 (Larkin et al., Transgenic Research 5(5):325–335 (1996); seed albumin gene from sunflowers (Khan et al, Transgenic Research 5(3):179–185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra).

Other transgenes of interest include, but are not limited to, those coding for or related to lignin content, cellulose content, nitrogen fixation, improved nutrition, color, vitamin content and recombinantly produced vaccines.

D. Site-Specific Recombination Systems

Methods and constructs for targeting of DNA sequences for insertion into a particular DNA locus, while enabling removal of randomly inserted DNA sequences that occur as a by-product of transformation procedures, are described in U.S. Pat. Nos. 5,527,695 and 6,114,600. One manner of removing these random insertions is to utilize a site-specific recombinase system. In general, a site-specific recombinase system consists of three elements: two pairs of DNA sequence (the site-specific recombination sequences) and a specific enzyme (the site-specific recombinase). The site-specific recombinase will catalyze a recombination reaction only between two site-specific recombination sequences.

A number of different site-specific recombinase systems can be used, including but not limited to the Cre/lox system of bacteriophage P1, the FLP/FRT system of yeast, the Gin recombinase of phage Mu, the Pin recombinase of *E. coli*, and the R/RS system of the pSR1 plasmid. The two preferred site-specific recombinase systems are the bacteriophage P1 Cre/lox and the yeast FLP/FRT systems. In these systems a recombinase (Cre or FLP) will interact specifically with its respective site-specific recombination sequence (lox or FRT respectively) to invert or excise the intervening sequences. The sequence for each of these two systems is relatively short (34 bp for lox and 47 bp for FRT). Currently the FLP/FRT system of yeast is the preferred site-specific recombinase system since it normally functions in a eukaryotic organism (yeast), and is well characterized. It is thought that the eukaryotic origin of the FLP/FRT system allows the FLP/FRT system to function more efficiently in eukaryotic cells than the prokaryotic site-specific recombinase systems.

The FLP/FRT recombinase system has been demonstrated to function efficiently in plant cells. Experiments on the performance of the FLP/FRT system in both maize and rice protoplasts indicates that FRT site structure, and amount of the FLP protein present, affects excision activity. In general, short incomplete FRT sites leads to higher accumulation of excision products than the complete full-length FRT sites. Site-specific recombination systems can catalyze both intra- and intermolecular reactions in maize protoplasts, indicating that the system can be used for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

E. Vectors

Expression Units to Express Exogenous DNA in a Plant

As provided above, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumafacians*. Alternatively, plant viral promoters can also be used, such as the cauliflower mosaic virus 35S promoter to control gene expression in a plant. Lastly, plant promoters such as prolifera promoter, fruit-specific promoters, Ap3 promoter, heat shock promoters, seed-specific promoters, etc. can also be used. The most preferred promoters will be most active in male or female gametes.

Either a gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium octopine* synthase signal (Gielen et al., *EMBO J.* 3:835–846 (1984)) or the nopaline synthase signal (Depicker et al., Mol. and Appl. Genet. 1:561–573 (1982)).

The resulting expression unit is ligated into or otherwise constructed to be included in a vector that is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as ampicillin, kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 Arabidopsis thaliana ESTs have been produced by a French and an American consortium (Delseny et al., FEBS Lett. 405(2):129–132 (1997); Arabidopsis thaliana Database, http://genome.www.stanford.edu/Arabidopsis). For a discussion of the analysis of gene-expression patterns derived from large EST databases, see, e.g., M. R. Fannon, TIBTECH 14:294–298 (1996).

Biologically compatible fluorescent protein probes, particularly the self-assembling green fluorescent protein (GFP) from the jellyfish *Aequorea Victoria*, have revolutionized research in cell, molecular and developmental biology because they allow visualization of biochemical events in living cells (Murphy et al., Curr. Biol. 7(11):870–876 (1997); Grebenok et al., Plant J. 11(3):573–586 (1997); Pang et al., Plant Physiol 112(3) (1996); Chiu et al., Curr. Biol. 6(3):325–330 (1996); Plautz et al., Gene 173(1):83–87 (1996); Sheen et al., Plant J. 8(5):777–784 (1995)).

Site-directed mutagenesis has been used to develop a more soluble version of the codon-modified GFP called soluble-modified GFP (smGFP). When introduced into Arabidopsis, greater fluorescence was observed when compared to the codon-modified GFP, implying that smGFP is 'brighter' because more of it is present in a soluble and functional form (Davis et al., Plant Mol. Biol. 36(4):521–528 (1998)). By fusing genes encoding GFP and beta-glucuronidase (GUS), researchers were able to create a set of bifunctional reporter constructs which are optimized for use in transient and stable expression systems in plants, including Arabidopsis (Quaedvlieg et al., Plant Mol. Biol. 37(4):715–727 (1998)).

Berger et al. (Dev. Biol. 194(2):226–234 (1998)) report the isolation of a GFP marker line for Arabidopsis hypocotyl epidermal cells. GFP-fusion proteins have been used to localize and characterize a number of Arabidopsis genes, including geranylgeranyl pyrophosphate (GGPP) (Zhu et al., Plant Mol. Biol. 35(3):331–341 (1997).

Disabling Genes

An example of an effective disabling modification would be a single nucleotide deletion occurring at the beginning of a gene that would produce a translational reading frameshift. Such a frameshift would disable the gene, resulting in non-expressible gene product and thereby disrupting functional protein production by that gene. If the unmodified gene encodes a protease, for example, protease production by the gene could be disrupted if the regulatory regions or the coding regions of the protease gene are disrupted.

In addition to disabling genes by deleting nucleotides, causing a transitional reading frameshift, disabling modifications would also be possible by other techniques including insertions, substitutions, inversions or transversions of nucleotides within the gene's DNA that would effectively prevent the formation of the protein encoded by the DNA.

It is also within the capabilities of one skilled in the art to disable genes by the use of less specific methods. Examples of less specific methods would be the use of chemical mutagens such as hydroxylamine or nitrosoguanidine or the use of radiation mutagens such as gamma radiation or ultraviolet radiation to randomly mutate genes. Such mutated strains could, by chance, contain disabled genes such that the genes were no longer capable of producing functional proteins for any one or more of the domains. The presence of the desired disabled genes could be detected by routine screening techniques. For further guidance, see U.S. Pat. No. 5,759,538.

Antisense Encoding Vectors

Methods for inhibiting expression in plants using antisense constructs, including generation of antisense sequences in situ are described, for example, in U.S. Pat. Nos. 5,107,065; 5,254,800; 5,356,799; 5,728,926; and 6,184,439. The later two patents being entitled: "Antisense gene systems of pollination control for hybrid seed production".

Other methods that can be used to inhibit expression of an endogenous gene in a plant may also be used in the present methods. For example, formation of a triple helix at an essential region of a duplex gene serves this purpose. The triplex code, permitting design of the proper single stranded participant is also known in the art. (See H. E. Moser, et al., Science 238:645–650 (1987) and M. Cooney, et al., Science 241:456–459 (1988)). Regions in the control sequences containing stretches of purine bases are particularly attractive targets. Triple helix formation along with photo-crosslinking is described, e.g., in D. Praseuth, et al., Proc. Nat'l Acad. Sci. USA 85:1,349–1,353 (1988).

II. Transformation

A. Plant Transformation

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can than be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome.

Homologous recombination and site-directed integration in plants are discussed in U.S. Pat. Nos. 5,451,513; 5,501,967 and 5,527,695.

B. Transformation Methods

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765; 5,472,869; 5,538,877; 5,538,880; 5,550,318; 5,641,664; 5,736,369 and 5,736369; Watson et al., Recombinant DNA, Scientific American Books (1992); Hinchee et al., Bio/Tech. 6:915–922 (1988); McCabe et al., Bio/Tech. 6:923–926 (1988); Toriyama et al., Bio/Tech. 6:1072–1074 (1988); Fromm et al., Bio/Tech. 8:833–839 (1990); Mullins et al., Bio/Tech. 8:833–839 (1990); and, Raineri et al., Bio/Tech. 8:33–38 (1990)).

Transgenic alfalfa plants have been produced by many of these methods including, but not limited to, agrobacterium-mediated transformation (Wang et al., Australian Journal of Plant Physiology 23(3):265–270 (1996); Hoffman et al., Molecular Plant-Microbe Interactions 10(3):307–315 (1997); Trieu et al., Plant Cell Reports 16:6–11 (1996)) and particle acceleration (U.S. Pat. No. 5,324,646).

Transformation has also been successfully accomplished in clover using agrobacterium-mediated transformation (Voisey et al., Biocontrol Science and Technology 4(4):475–481 (1994); Quesbenberry et al., Crop Science 36(4):1045–1048(1996); Khan Plant Physiology 105(1):81–88 (1994); Voisey et al., Plant Cell Reports 13(6):309–314 (1999)).

Genetic transformation has also been reported in numerous forage and turfgrass species (Conger B. V. Genetic Transformation of Forage Grasses in Molecular and Cellular Technologies for Forage Improvement, CSSA Special Publication No. 26, Crop Science Society of America, Inc. E. C. Brummer et al. Eds. 1998, pages 49–58). These include orchardgrass (*Dactylis glomerata* L.), tall fescue (*Festuca arundinacea* Schreb.) red fescue (*Festuca rubra* L.), meadow fescue (*Festuca pratensis* Huds.) perennial ryegrass (*Lolium perenne* L.) creeping bentgrass (*Agrostis palustris* Huds.) and redtop (*Agrostis alba* L.).

Successful gene transfer in such forages and turfgrasses has been accomplished by direct uptake of DNA by protoplasts and by bombardment of cells or tissues with DNA coated microprojectiles. In both cases, the transfer is followed by whole plant regeneration. Much of the work has focused on developing and improving protocols for the transformation and have used the reporter gene uidA coding for—glucouronidase (GUS) and the selectable marker bar that confers tolerance to phosphinothricin-based herbicides. Proof of the transformation has been provided by polymerase chain reaction (PCR) techniques, northern hybridization analysis of transcribed RNA, western blot analysis of soluble protein (gene product), and southern blot hybridization of total genomic DNA.

III. Hemizygosity

A transgenic plant formed using Agrobacterium transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and test-crossing of the F2 progeny to non-transformed control plants can be used to identify homozygous transgenic plants and to maintain the line. If the progeny initially obtained for a regenerated plant were from cross pollination, then identification of homozygous transgenic plants will require an additional generation of self-pollination (U.S. Pat. No. 5,545,545).

IV. Semi-Sterility and Genetic Sterility Filter

A. The Gametophytic Sterility Trait (GST)

The GST can be composed of two or three elements: a sex-specific promoter, a suicide gene and, optionally, a region encoding a transposon and/or transposase. Normally, the GST construct ends in a transcription terminator element. The inclusion of a transposon or a transposase source is specific to the application of selecting for dispersed transpositions and not necessarily used for the purposes of eliminating transmission of transgenes.

Sex-specific promoters that may be used include but are not limited to: pollen-specific promoters from maize, rice, tomato, tobacco, Arabidopsis and Brassica. Several other examples can be found in GenBank. The promoter must be specific to one sex (male or female) and specifically drive gene expression after meiosis I when homologous chromosomes have separated into different cells.

The suicide gene is used to kill unwanted meiotic products. Suicide genes include but are not limited to: barnase, tasselseed2 and the diphtheria toxin A gene. Two alternatives to using a suicide gene include 1) using antisense RNA technology to inhibit expression of genes essential to the viability of the pollen or the egg; or 2) mutations that are incapable of transmission through one of the sexes, such as deletions that are not pollen-transmitted. Both of these alternatives can be used to achieve semi-sterility.

B. Semi-Sterility and Genetic Sterility Filter

The terms "semi-sterility" and "genetic sterility filter" are used by the inventors to convey the idea that since suicide gene expression is confined to post-meiosis I, only 50% of gametes will be eliminated when the GST locus is hemizygous and segregates normally in meiosis. This is due to the fact that when the GST locus is present in the genome in a single copy (hemizygous condition), the suicide gene will be transmitted to approximately one-half of the products of meiosis, resulting in a 50% sterility rate. Pollen inheriting the GST will not survive if a pollen specific promoter is operably linked to the suicide gene.

The production of 50% viable pollen is necessary for the recovery of dispersed transpositions and/or to prevent transgene transmission without a major effect on male fertility.

C. Gametophytic Semi-Sterility

The current invention describes the use of a technology that utilizes gametophytic "semi-sterility", such as pollen semi-sterility, to generate a "genetic sterility filter" that eliminates gametes that inherit a specific transgene complex. Incorporation of a pollen-specific promoter into the GST prevents the transmission of transgenes linked to the GST in pollen inheriting this transgene complex.

This transgene complex may also contain a launching site for a transposable element and/or transposase gene. In this case, the elimination of the transgene complex, along with the transposon donor site and/or transposase, has the net effect of eliminating nearby transpositions while enriching for transposition events that have recombined with the transgene complex or that are dispersed (no longer linked to the GST) throughout a genome. This methodology overcomes several current limitations of transposon mutagenesis strategies that favors mostly localized over dispersed transpositions. The invention greatly improves on the current use of negative selectable markers to achieve transposon dispersion (Sundaresan, V., et al., (1995) Genes Dev. 9/14:1797–810; Tissier, A. F. et al., (1999) The Plant Cell Vol. 11:1841–1852). Moreover, the use of the genetic sterility filter to eliminate transmission of a transposase source stabilizes the newly transposed elements in progeny, thereby eliminating somatic or secondary transposition events that hamper mutation identification.

The nature of the semi-sterility trait and its associated transposon and/or transposase, may differ in details depending on the choice of suicide genes, promoters, transposon systems, and species. It is emphasized, however, that the same basic technology of semi-sterility can be used to recover transpositions in many plants, both monocots and dicots, in such species such as maize, rice, soybeans, wheat, oats, barley, and in non-plant systems, such as animals and fungi, that can be sexually propagated. Furthermore, an alternative strategy to microspore elimination is to eliminate female transmission of the transgene complex by engineering a megaspore suicide trait.

The semi-sterility trait is used to eliminate the products of meiosis (gametes) that carry a particular chromosomal region, such as a transposon launching site and/or transposase gene. This "genetic sterility filter" is used to eliminate male or female transmission of a transgene complex. This elimination process has the net effect of enriching for unlinked (dispersed) transposed elements or elements that recombined from the launching site; it is also used to simultaneously eliminate transmission of other genes, such as a transposase gene, thereby stabilizing transpositions in progeny. To achieve semi-sterility, a number of preferred methods are contemplated by the instant invention. One method relies on directing microspore-specific expression of a suicide gene to kill unwanted microspores. This method is achieved by employing a specific promoter, such as a pollen-specific promoter, fused to an appropriate suicide gene, thereby killing only the products of meiosis that have inherited the gene fusion. For a single copy transgene in hemizygous condition, this represents 50% of the gametes. Because pollen is produced in large excess, reducing pollen fertility by 50% has no major consequence on subsequent seed production.

The aspect of the current invention relating to generating semi-sterility differs from previous methods aimed at achieving full male-sterility for hybrid seed production that are known in the art. In these methods, the aim has been to achieve complete male sterility to facilitate the commercial production of hybrid seed. This usually involves expression of the suicide gene in the sporophyte or in all microspores. For instance, barnase expression in tapetal cells results in complete male sterility (Beals, T. P. et al. (1997) The Plant Cell. Vol. 9:1527–45). In hybrid seed production, pollen semi-sterility would be insufficient to achieve the desired result, i.e. outcrossing of male-sterile (female) parent. In cases where a microspore-specific suicide gene and its associated elements are present in the genome in a single copy (in hemizygous condition), the suicide gene will be transmitted to approximately one-half of the products of meiosis, resulting in an average of 50% semi-sterility, a rate of viable pollen production that is commercially unacceptable for hybrid seed production. For the present invention, the production of 50% viable pollen is necessary and important to recover dispersed transpositions and/or to prevent transposase transmission. Hence, the gametophytic sterility trait is used as a filter to eliminate undesirable genomes while at the same time allowing other genomes (non-transgenic and genomes containing transposed elements without the donor element and/or transposase gene present) to be transmitted. In one embodiment, the present invention makes us of this "genetic sterility filter" to eliminate a transgene complex containing a transposon launching site and/or transposase source.

V. Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100–200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161–176, *In Hybridization of Corp Plants*, supra.

VI. Transposons and Transposable Elements

Transposons are genetic elements capable of transposition (movement) from a donor chromosomal site to a target site on the same chromosome or different chromosome. Transposons cause mutations by insertion into coding sequences, introns, and promoters, often completely eliminating target gene activity. Mutations caused by transposons can often be destabilized by subsequent excision of the transposon from the gene. One or more proteins, collectively referred to as "transposase", are required for the excision and integration of the transposon. Transposons that encode their own source of transposase are referred to as autonomous elements. Supplying transposase in trans can transpose transposons that do not encode transposase but contain terminal sequences, usually inverted repeats, required for transposition (non-autonomous elements).

A. Ds Elements

In one of the preferred embodiments, a Ds element is contemplated such that it contains the terminal sequences required for transposition (Coupland, G., et al., (1989) Proc Natl Acad Sci USA 86:9385–8; Chatterjee, S. et al., (1995) Mol Gen Genet. 249:281–8), a minimal promoter (-47 CaMV 35S promoter) fused to GUS reporter gene for enhancer detection; in opposite orientation, a splice acceptor site fused to an enhanced fluorescent, dual-spectrum GFP gene (Haseloff, J., et al., (1997) Proc Natl Acad Sci USA. 94:2122–7; Haseloff, J., et al., (1999) Methods Mol Biol. 122:241–59; Haseloff, J. (1999) Methods Cell Biol. 58:139–51) for gene trapping purposes. This Ds element can be used to screen for enhancer traps in one insertion orientation or gene traps in the other orientation, with respect to target gene transcription. A second embodiment using Ds substitutes a transcriptional activator at one end of the Ds element in order to generate gain-of-function mutations. Both elements contain a lox P site for site-specific recombination (Osborne, B.I., et al., (1995) 7:687–701; Medberry, S. L., et al., (1995) Nucleic Acids Res. 23:485–90; Qin, M., et al., (1994) Proc Natl Acad Sci USA 91:1706–10) and the bar gene Thompson, C. J., et al., (1986) EMBO J. 6:2519–23) for herbicide (Finale®) for tissue culture and soil selection. Finale® is the registered trademark of a glufosinate herbicide.

B. Utility of Transposon and Insertion Mutations in Plants

Transposons have great utility in genetic analysis and functional genomic analysis of bacterial, fungal, plant and animal genomes. In plants, genetically engineered transposons have been successfully introduced into several species (for review see Sundaresan, V, (1996) Trends Plant Sci. Vol. 1:184–190) including rice (Izawa, T. et al., (1997) Plant Mol Biol Vol. 35/1–2:219–29), tobacco, Arabidopsis, lettuce and several others. Several investigators have come up with ingenious methods to enhance the efficiency of recovering transposition events, including methods for positive selections for transposition (Fedoroff, N. V. et al., (1993) Plant J. Vol.:3:273–289; Honma, M. A. et al., (1993) Proc Natl Acad Sci USA Vol. 90/13:6242–6), selection for unlinked elements, (Tissier et al., (1999) The Plant Cell Vol. 11:1841–1852; W. R.; Sundaresan, et al., (1995) Genes Dev. 9/14:1797–810), dispersed launching sites throughout a genome (Cooley, M. B. et al., (1996) Mol Gen Genet Vol. 252/1–2:184–94, Knapp, S. et al., (1994) Mol Gen Genet Vol. 243/6:666–73; Osborne, B. I. et al., (1991) Genetics Vol. 129/3:833–44; Takken, F. L. et al., (1998) Plant J Vol. 14/4:401–11, Thomas, C. M, et al., (1994) Mol Gen Genet Vol. 242/5:573–85; van der Biezen, E. A. et al., 1996 Mol Gen Genet Vol. 251/3:267–80) and adding features into elements such as enhancer and gene traps (for reviews see Sharknes, W. C., (1990) Biotechnology 8:827–831; W. R.; Sundaresan, et al., (1995) Genes Dev 9/14:1797–810) and transcriptional activation (Fritze, K. et al. (1995) Methods Mol Biol Vol. 44:281–94; Kakimoto, T., (1996) Science Vol. 274/5289:982–5; Kardailsky, I.; et al, (1999) Science Vol. 286/5446:1962–5).

Even given the enormous progress in the utility of transposons, they still have limitations for functional genomic analysis. Transpositions are often intrachromosomal, often within a short physical distance between donor and target sites (Moreno, M. A et al., (1992) Genetics Vol. 131:939–956; Athma, P. et al., (1992) Genetics Vol. 131:199–209). This limitation means that most new insertions occur in regions surrounding the donor site (launching site) with many fewer elements found dispersed randomly throughout the genome. Secondly, the process of transposition is not usually controlled leading to a great many somatic insertions, which are not transmitted to progeny, and developmentally early transpositions that can lead to non-concordance in germinally transmitted events. The inability to control transpositions somatically and temporally can result in a high background of false positive insertions in genes of interest due to the non-correspondence between somatic and germinal mutational events.

C. Current State-of-the-Art Methods to Recover Dispersed Transpositions

Two methods are currently available to partially overcome the limitation of non-dispersed transpositions. One method makes use of first dispersing transposon launching sites throughout a genome. This method, however, requires a large number of transgenic starter lines to achieve widespread genome coverage. A second method to disperse transposition events is to employ a negative selectable marker(s), such as iaaH, pehA, R404, or a cytosine deaminase gene, to select against the donor site containing the transposon and/or transposase. Selection against the donor element also selects against nearby (linked) transpositions resulting in enrichment for unlinked transpositions. Negative selections have been used in Arabidopsis to recover unlinked Ds and Spm transpositions (W. R.; Sundaresan, et al., (1995) Genes Dev. 9/14:1797–810; Tissier, A. F., et al., (1999) The Plant Cell Vol. 11:1841–1852) and two negative selectable markers are based on proherbicide conversion (O'keefe, D. P. et al., (1994) Plant Physiol Vol. 105:473–482; Dotson, S. B. et al., (1996) The Plant Journal Vol. 10/2:383–392), a process theoretically amenable to soil selections.

Nevertheless, the use of negative selectable markers imposes serious limitations on the recovery of large numbers of independent transpositions. First, several of these markers require the use of tissue-culture based (W. R.; Sundaresan, et al., (1995) Genes Dev. 9/14:1797–810; transposition (Fedoroff, N. V. et al., (1993) Plant J. Vol.:3:273–289), a labor-intensive procedure that adds great expense and time to the process of recovering large numbers of dispersed transpositions. Second, negative selections are based on the elimination of progeny carrying linked elements or transposase, or both, by chemical (Tissier, A. F., et al., (1999) The Plant Cell Vol. 11:1841–1852; W. R.; Sundaresan, et al., (1995) Genes Dev. 9/14:1797–810). Progeny elimination can be problematic when seed number is limited. For instance, in a plant such as rice (*Orza sativa*), a predominantly self-pollinating species, outcrossing is tedious and time-consuming, greatly limiting the number of progeny that can be readily obtained. Hence, if transposition rates are low and unlinked transpositions represent the minority of transposition events, it would be costly and impractical to use negative selections to recover dispersed transpositions. For instance, accounting for a rate of 1–5% transposition, 50% meiotic segregation, and only 30% unlinked transpositions, to recover 10,000 transpositions by outcrossing would require an estimated several million progeny plants. Finally, the use of negative selectable agents, such as proherbicides, can have a serious environmental impact and be costly due to the applications of chemicals that may be needed to select for large numbers of progeny carrying dispersed transpositions. Moreover, most of these chemicals are not approved for field use.

VII. Transposase

Florally Expressed Transposase

A further limitation associated with using transposons for mutagenesis, gene-tagging and functional genomic analysis, is the lack of developmental and temporal control over the transposition process. In most cases transposase gene expression, under the control of its own promoter, or under the control of constitutive promoters, occurs during vegetative development of the plant. Vegetative expression of a transposase source leads to somatic transpositions. These transpositions are transmitted to progeny (germinal transpositions) only when these somatic cell lineages later produce megaspores or microspores. This is problematic for two reasons. One reason is that transpositions that occur during vegetative or early reproductive development can be clonally propagated and later transmitted into many gametes, resulting in a large number of non-independent elements recovered in progeny. This is undesirable when large numbers of independent transpositions are needed for functional genomic analysis or gene-tagging. Second, somatic transpositions often do not include lineages that give rise to gametes, such as those occurring in epidermal lineages or in terminal vegetative structures. These transpositions are never meiotically transmitted and therefore go unrecovered in progeny. This is problematic because these somatic events can be falsely identified in tissue DNA samples as mutations, yet are never recovered in progeny. This is especially problematic when mutational screens are PCR-based examples chemical (Tissier, A. F., et al., (1999) The Plant Cell Vol. 11:1841–1852; McKinney, E. C., et al., (1995) Plant J. Vol. 8:613–622; Krysan, P. J et al., (1996) Proc. Natl. Acad. Sci. USA Vol. 93:8145–8150; Frey, M et al., (1997) Science Vol. 277:696–699).

In a further embodiment of the instant invention, to minimize the problem of somatic transpositions, a transposase gene is placed under the control of a floral-specific promoter that drives gene expression in subepidermal lineages of the flower that lead to the production of microspores and megaspores. Such promoters include those found in genes such as agamous, apetalal apetala2, apetala3, pistillate, and their homologs found in other plant species such as maize, and rice. For example, the apetala3 promoter drives expression of a reporter gene in petal and sepal primordial cells of the developing floral meristems. Transposase expression under the control of the ap3 promoter results in transpositions that are confined to floral development and, when occurring in lineages that give rise to microspores, these events will be transmitted to the next generation. Control of transposition by this method has two effects: 1) it shuts down somatic transpositions; and 2) it leads to a large number of independent transpositions when pollen is derived from many different floral meristems. Hence, somatic tissue can be sampled without the concern of somatic or secondary transpositions, and each floral meristem becomes an independent source of transposition events.

VIII. Rice—A Model Plant System

A. Rice Agriculture in the US and Worldwide

Approximately half of the world's population derives its caloric intake mainly from rice. Annual worldwide production levels are over 400 million metric tons, grown on over 200 million hectares (Anonymous (2000) USDA World Agriculture Supply and Demand Estimates. USDA Agricultural Marketing Service. Publication WASDE-362).

At present, the U.S. produces 7.5 million metric tons of rice per year, planted on 1.4 million hectares, resulting in $1.7 billion dollars in commerce (Anonymous (2000) USDA World Agriculture Supply and Demand Estimates. USDA Agricultural Marketing Service. Publication WASDE-362). More than two-thirds of the rice produced in this country is exported to markets, mainly in Asia and Latin America, making the U.S. the third largest exporter worldwide.

Approximately 99% of the rice varieties currently grown are the result of public breeding programs, many originating from breeding programs sponsored by CGIAR international research centers such as International Rice Research Institute (IRRI) and International Center for Tropical Agriculture (CIAT). The majority of U.S. rice varieties are developed in the states of Arkansas, Louisiana, Mississippi, Texas and California. Agricultural biotechnology is becoming increasingly important to develop modern varietal rice lines; biotechnology development is expected to greatly assist the U.S. rice farmers competing in this global marketplace B. Rice as a Model System for Monocot Development Cereals include the most important food crops in the world, and are considered a relatively recent taxon, evolving from a common ancestor only 65 million years ago (Martin, W., et al., (1989) Nature 339:46–48; Moore, G., et al., (1995) Trends Genet. 11:81–82). This young history is reflected in a remarkable degree of conservation in gene structure and order even though differences have arisen in genome size, haploid chromosome number, and variations in repetitive sequence composition (Moore, G., et al., (1993) Bio/technology. 11:584–589). For example, the maize genome is 8-fold larger than that of rice (Ahn, S. et al., (1993) Genetics 90:7980–7984) and organized into a different number of chromosomes, yet comparative molecular analysis has shown that extensive synteny can be identified between much of their genomes (Ahn, S. et al., (1993) Genetics. 90:7980–7984; Bennetzen, J. L. et al., (1993) Trends Genet. 9:259–261).

Rice is an outstanding model plant for the cereal grasses. Rice can be used to investigate basic biological issues and to learn about agronomic traits such as yield, hybrid vigor, and single and multigenic disease resistance. Different races of rice are adapted to a wide variety of environmental situations, from tropical flooding to temperate dry land, so it is a model for real life adaptive responses.

Rice has a relatively short generation time (90–120 days), making it possible to obtain three or more generations per year. A large collection of mutations have been discovered and characterized in rice.

Transgenic rice is efficiently generated by either Agrobacterium-mediated (Hiei, Y., et al., (1994) Plant J. 6:271–82; Hiei, Y., et al, (1997) Plant Molec Bio. 35:205–218; Zhang, J., et al., (1997) Mol Biotechnol. 8:223–31) or biolistic methods (Christou, P., et al., (1991) Biotechnology. 9:957–962; Buchholz, W. G., et al., (1998) Methods Mol Biol. 81:383–96). Most importantly, rice has a genome size approximately 500 megabases (Mb) (Arumanagathan, K. et al., (1991) Plant Mol. Biol. Report. 9:208–218), only about 3-fold larger than that of the Arabidopsis genome, and scheduled to be sequenced around 2004. As a member of the Graminae and an important crop plant, a wealth of fundamental information about important aspects of plant biology can be learned from the rice genomics (McCouch, S. (1998) Proc. Natl. Acad. Sci. USA 95:1983–5; Wilson, W. A., et al., (1999) Genetics. 153:453–73).

C. Rice Genomics

Rice is one of the most densely mapped plant genomes (McCouch, S. R., et al., (1997) Plant Mol Biol. 35:89–99; Panaud, O., et al., (1996) Mol Gen Genet. 252:597–607). The two best-developed recombinational maps are those developed at Cornell and at the Rice Genome Project (RGP) in Japan, on which more than 3,000 RFLP and SSR markers have been mapped. The YAC-based physical map of rice covers more than 64% of the genome and contains 4,000 mapped ESTs (Ashikawa, I., et al., (1999) Genome. 42:330–7). A PAC library of 71,000 clones has been mapped with STSs and ESTs and the mapped clones cover approximately 30% of the genome. Two BAC libraries with 37,000 and 55,000 members have been BAC-end sequenced and finger printed and a BAC-based physical map has been constructed.

The rice genome is estimated to contain 500 Mb (Arumanagathan, K. et al., (1991) Plant Mol. Biol. Report. 9:208–218) and 340,000 genes. The International Rice Genome Sequencing Project was formed in 1998 to obtain the complete genome sequence of *Oryza sativa* ssp. japonica cv. Nipponbare. Ten countries are collaborating in this effort. Currently about 10 Mb have been submitted to Genbank.

D. Utility of a Transposon-Based Genomics Program

The main justification for the use of transposons is their distinct advantage over other types of mutagens for functional genomic studies. In rice, T-DNA and retrotransposon mutagenesis have serious limitations. Currently, both methods require continual tissue culture selection and somatic regeneration to recover insertions, processes that are inefficient, time-consuming and prone to induction of somaclonal variation (Bao, P. H., et al. (1996) Transgenic Res. 5:97–103; Evans, D. A. (1989) Trends Genet. 5:46–50). Both agents generate only stable insertions, which subsequently limit the utility of any mutant allele. To further complicate matters, T-DNA insertions are often large, complex tandem arrays, causing difficulties with molecular analysis of mutant alleles (McKinney, E. C., et al., (1995) Plant J. 8:613–622; Krysan, P. J., et al., (1996) Proc. Natl. Acad. Sci. USA 93:8145–8150; Krysan, P. J., et al., (1999) Plant Cell. 11:2283–2290; Galbiati, et al., (2000) Functional & Integrative Genomics, in press).

In many instances, single loss-of-function mutations, such as T-DNA- or retrotransposon-induced alleles, will not provide sufficient information to derive gene function. For instance, based on limited studies to date, many gene disruptions do not produce a readily discernable phenotype (McKinney, E. C., et al., (1995) Plant J. 8:613–622; Krysan, P. J., et al., (1996) Proc. Natl. Acad. Sci. USA 93:8145–8150). This does not imply lack of gene importance, however, since many of these genes will have partially redundant, overlapping or specific functions not detectable based on morphological or developmental screening of mutant lines. More detailed information, such as expression analysis and additional alleles, will be necessary.

On the other hand, two-element transposon mutagenesis, such as the Ac/Ds system, can generate stable gene disruptions by simple insertion. Genetically engineered Ds elements have been successfully introduced into several plant species (for review see Martienssen, R. A. (1998) Proc. Natl. Acad. Sci. USA 95:2021–6; Sundaresan, V. (1996) Trends Plant Sci. 1:184–190) including rice (Izawa, T., et al. (1997) Plant Mol Biol. 35:219–29).

The utility of transposons for functional genomics has been greatly enhanced by building features into synthetic transposons such as enhancer and gene traps (for reviews see Martienssen, R. A. (1998) Proc. Natl. Acad. Sci. USA 95:2021–6; Sharknes, W. C. (1990) Biotechnology 8:827–831; Sundaresan, V., Springer, et al., (1995) Genes Dev. 9:1797–810) and transcriptional activation (Fritze, K. et al., (1995) Methods Mol Biol. 44:281–94; Kakimoto, T. (1996) Science. 274:982–5; Kardailsky, I., et al., (1999) Science. 286:1962–5). By incorporating such features, even genes that are genetically redundant can be functionally analyzed. Most importantly, the ability to remobilize a transposon creates the unique opportunity to efficiently generate derivative alleles and to efficiently mutate nearby genes by localized transposition properties of these elements (Long, D., et al., (1997) Plant J. 11:145–8; Jones, J. D. G., et al., (1990) Plant Cell. 2:701–707; Osborne, B. I., et al., (1991) Genetics. 129:833–44). Starting with a just a few, well-characterized transgenic lines and the appropriate genetic strategies, an extensive collection of dispersed transpositions can be efficiently generated without the need for subsequent tissue culture selection or regeneration.

E. Randomly Dispersing Ds Throughout the Rice Genome

The present invention includes methods that may be applied to specific genomes, including but not limited to, the rice genome. Rice is an outstanding model plant for the cereal grasses. In applying the methods of the instant invention to the rice genome, one goal is to produce an extensive collection of stable Ds insertions that are distributed throughout the rice genome. To accomplish this task, several genetic strategies are contemplated, with the main goals of minimizing non-independent transpositions, dispersed Ds transpositions throughout the rice genome, and stabilized transposed elements in progeny. A specific strain contemplated for use in the methods of the instant invention is *Oryza sativa* ssp. *japonica cv*. Nipponbare, the strain being sequenced by the IRGSP.

In one embodiment of the instant invention, randomly dispersing Ds throughout the rice genome is contemplated. Because Ds tends to transpose locally often over short genetic distances, genetic strategies must be used to counter this bias. In the past, this has been accomplished using various methods that basically involve selecting against the Ds launching site in progeny (Sundaresan, V., et al., (1995) Genes Dev. 9:1797–810; Tissier, A. F. et al., (1999) The Plant Cell 11:1841–1852), orby initially dispersing many launching sites throughout a genome (Osborne, B. I., et al., (1991) Genetics. 129:833–44; Cooley, M. B., et al., (1996) Mol Gen Genet. 252:184–94; Knapp, S., et al., (1994) Mol Gen Genet. 243:666–73; Takken, F. L., et al., (1998) Plant J. 14:401–11; Thomas, C. M., et al., (1994) Mol Gen Genet. 242:573–85; van der Biezen, E. A., et al., (1996) Mol Gen Genet. 251:267–80).

Two strategies for dispersing Ds transpositions are contemplated. The first method is broadly directed to including a pollen-specific suicide trait gene on the Ds launching site to eliminate transmission of the launching site along with any linked transposed elements. The suicide trait is engineered by incorporating a pollen-specific promoter driving expression of an appropriate cell death gene. Since the launching site construct is single copy and hemizygous in stock plants, 50% of the products of meiosis inherit T-DNA and undergo genetic suicide; the remaining products produce viable pollen. Those transposed Ds that have recombined, either intra- or inter-chromosomally with the launching site, are pollen transmitted. These elements are readily detected in progeny by incorporating an herbicide marker (bar gene) into the Ds element. The herbicide marker serves a dual purpose-as an initial tissue-culture selectable marker for rice transformation, and later as a soil-based selection for progeny harboring unlinked Ds elements.

The pollen suicide method has distinct advantages over previous strategies to select for unlinked transpositions. Its main advantage is that pollen is produced in vast excess and pollen semi-sterility is environmentally sound and will have little, if any, impact on seed production. In progeny, 50% of the testcross offspring (or 75% when selfing) are culled by negative selection simply because they inherit the launching site (and/or transposase gene, as explained below). In rice, when outcrossing is required to recover transpositions, seed production can be a limiting factor. Moreover, chemicals, such as proherbicides used for negative selection (Tissier, A. F., et al., (1999) The Plant Cell. 11:1841–1852; Dotson, S. B., et al., (1996) The Plant Journal. 10:383–392) are neither commercially available nor federally approved for field use. Tissue culture based negative selections (Sundaresan, V., et al., (1995) Genes Dev. 9:1797–810; Kobayashi, T., et al., (1995) Jpn J. Genet. 70:409–22) are impractical in rice.

In one embodiment of the instant invention, the pollen-specific suicide trait is engineered using an appropriate promoter driving the expression of a suicide gene. Several suicide genes are available, including the barnase gene (Goldman, M. H., et al., (1994) EMBO J. 13:2976–84), related RNases (Fedorova, N. D., et al., (1994) Mol Biol (Mosk). 28:468–71), diphtheria toxin A chain gene (Tsugeki, R. et al., (1999) Proc Natl Acad Sci USA. 96:12941–6; Nilsson, O., et al., (1998) Plant J. 15:799–804; Uk Kim, et al., (1998) Mol Cells. 8:310–7; Day, C. D., et al., (1995) Development 121:2887–95) and others (DeLong, A., et al., (1993) Cell. 74:757–768). Use of the barnase gene has been shown to be an effective way to generate microspore-autonomous cell death when fused to a pollen-specific promoter (Custers, J. B., et al., (1997) Plant Mol Biol. 35:689–99). In contrast to previous methods, the methods of the instant invention depend on generating semi-sterility, as opposed to complete male sterility, which may be achieved in one aspect of the present invention by engineering barnase expression specifically in microspores. Several promoters are available for this purpose, including both rice (Zou, J. T., et al., (1994) Amer. J. Botany. 81:552–561) and maize pollen-specific promoters (Hamilton, D. A., et al., (1992) Plant Mol Biol. 18:211–8), and pollen-specific promoters from several dicotyledonous species (Twell, D., et al., (1991) Genes Dev. 5:496–507; Kulikauskas, R. et al., (1997) Plant Mol Biol. 34:809–14; Custers, J. B., et al., (1997) Plant Mol Biol. 35:689–99; Albani, D., et al., (1991) Plant Mol Biol. 16:501–13; Kim, Y. et al., (1992) Transgenic Res. 1:188–94; Twell, D., et al.; (1990) Development. 109:705–13; van Tunen, A. J., et al., (1990) Plant Cell. 2:393–401). In a preferred embodiment, a heterologous pollen-specific promoter, such as the maize promoter (Hamilton, D. A., et al., (1992) Plant Mol Biol. 18:211–8), is contemplated to minimize the possibility of gene silencing.

Evaluation of the effectiveness of the pollen suicide mechanism in eliminating T-DNA (launching sites), may be achieved for example, by employing a construct containing the suicide gene and the bar gene transformed into an organism such as rice via Agrobacterium-mediated T-DNA transformation (Hiei, Y., et al., (1994) Plant J. 6:271–82; Hiei, Y., et al., (1997) Plant Molec Bio. 35:205–218; Zhang, J., et al.; (1997) Mol Biotechnol. 8:223–31). Several single copy T-DNA lines (SCTLs) would then be identified by Southern analysis (Ausebel, F. M., et al., (1987) In: *Current protocols in molecular biology*, ed. Chanda, V. B. Boston: John Wiley & Sons, Inc.). To test for the efficiency of T-DNA elimination, a PCR experiment would then be performed on unselected outcross progeny for detecting transmission of the T-DNA. This analysis would be performed on DNA pools from unselected progeny (e.g. a minimum of 384 DNA pools, each pool containing 12 plants). Using this evaluation procedure, it is contemplated that other constructs may be tested, such as those that include a transposase source (explained below), the pollen suicide gene, and the Ds-bar element.

F. Transposase Expression

A further embodiment of the instant invention is directed to enriching for independent transpositions while minimizing the recovery of non-independent ones. One way to accomplish this is by delaying transposition in development to prevent the early clonal propagation and meiotic transmission of non-independent events. Control over the developmental timing of transposition is achieved by using heterologous promoters driving the Ac transposase gene (Rommens, C. M., et al., (1992) Mol Gen Genet. 231:433–41; Balcells, L. et al., (1994) Plant Mol Biol. 24:789–98; Scofield, S. R., et al., (1992) Plant Cell. 4:573–82; Swinburne, J., et al., (1992) Plant Cell. 4:583–95; Grevelding, C., et al., (1992) Proc Natl Acad Sci USA. 89:6085–9). Several heterologous promoters are envisaged in the instant embodiment.

In a preferred embodiment the strategy to enrich for independent transpositions is to limit transposase expression exclusively to floral development, preferably excluding pistil expression (for reasons explained below), to prevent vegetative transpositions. A floral-specific promoter may be used to drive transposase expression during the formation of stamen primordia and several are available that preclude pistil expression such as rice (Moon, Y. H., et al., (1999) Plant Mol Biol. 40:167–77; Kang, H. G., et al., (1998) Plant Mol Biol. 38:1021–9; Greco, R., et al., (1997) Mol Gen Genet. 253:615–23) or maize MADS-box gene promoters (Mena, M., et al., (1996) Science 274:1537–40; Mena, M., et al., (1995) Plant J. 8:845–54). To enhance the frequency of transposition, both full-length cDNA and a truncated version of Ac transposase may be used in rice. The truncated version (ORF103-807) has been shown to enhance the frequency of transposition in heterologous plant species (Houba-Herin, et al., (1990) Mol Gen Genet. 224:17–23; Li, M. G. et al., (1990) Proc Natl Acad Sci USA. 87:6044–8).

Limiting transposase expression to floral development means that each floret represents an independent source of transpositions. Statistically, the recovery of non-independent transposition is low—if pollen from each anther is considered a source of independent transpositions then the frequency of progeny seed derived from pollen from the same anther will be unlikely—at least six times more anthers (six per spikelet) will be produced than seed (one per spikelet). Embodiments of the instant invention include the use of 35S-driven transposase (full-length and truncated) and florally-expressed transposase constructs transformed into rice along with a simple Ds element inserted into the 5' UTR of a bar gene. Single copy insert lines are then identified by Southern analysis and these plants are outcrossed to wild type, male-sterile IR36 females. Progeny seedlings are then subjected to two foliar applications of Finale® (see below) to select progeny in which Ds has excised. Based on the mechanism of Ac/Ds transposition (Chen, J., et al., (1987) Genetics. 117:109–116; Chen, J., et al., (1992) Genetics 130:665–676; Greenblatt, I. M. et al., (1962) Genetics. 47:489–501) more than 50% of these progeny contain linked or unlinked transposed Ds elements. Finale®-resistant progeny from each stock are analyzed by Southern analysis to determine the effectiveness of recovery of independent transpositions.

Once transposed, the Ds element needs to be stabilized, yet still have the ability to be remobilized. To stabilize transposed Ds elements, the appropriate transposase gene is included within the final T-DNA construct containing the Ds launching site. The pollen suicide process or bar antisense strategy eliminates the transposase source along with the T-DNA, thereby stabilizing any transposed Ds element in progeny. Reintroducing transposase in subsequent generations can easily destabilize the Ds element, permitting localized mutagenesis of neighboring genes (Long, D., et al., (1997) Plant J. 11:145–8; Ito, T., et al., (1999) Plant J. 17:433–44) or reconstitutional (saturation) mutagenesis (Moreno, M. A., et al., (1992) Genetics. 131:939–956; Athma, P., et al., (1992) Genetics. 131; Das, L. et al., (1995) Plant Cell. 7:287–94) of any single gene. cl EXAMPLES Example 1

Genetic Constructs pYU904—Synthetic Ds element

The synthetic Ds element was constructed by combining the 5' and 3' ends of Ac required for transposition. Primers P643 (aagctttggccatattgcagtcatcc) (SEQ ID NO:1) and P644 (aagcttgctcgagcagggatgaaagtaggatggga) (SEQ ID NO:2) are used to amplify the 5' end of the Activator element (Ac) from coordinates 4312 to 4565 bp (GenBank Accession X01380) (SEQ ID NO:3) while adding a Hind III cloning site to the 3' end and both a Hind III and Xho I site to the 5' end of the fragment. Primers P645 (gaattccctcgagtagggatgaaaacggtcggtaac) (SEQ ID NO:4)

and P646 (gaattcgaatatatgttttcatgtgtgat) (SEQ ID NO:5) are used to amplify the 3' end of the Ac element from coordinates 1 to 221 bp with the additional EcoRI and XhoI restriction sites were added to the 3' end of the fragment and an additional EcoRI restriction site was added to the 5' end of the fragment being amplified. These fragments were individually cloned in the vector pCR2.1-TOPO (Invitrogen).

Plasmid pYU890 contained the 5' end fragment of the Ac element, and plasmid pYU892 contained the 3' end fragment of the Ac element.

pYU892 was digested with EcoRI (New England Biolabs), and the 230 base pair (bp) Eco RI insert was cloned into the Eco RI site of pUC19 (GenBank Accession M77789) to generate pYU899.

pYU890 was digested with HindIII (New England Biolabs), and the 250 bp insert was subcloned into the HindIII site of plasmid pYU899 giving rise to plasmid pYU902. This plasmid contains the 5' and 3' ends of Ac, required for transposition, and an internal polylinker site for subsequent cloning purposes.

Figure 4A:
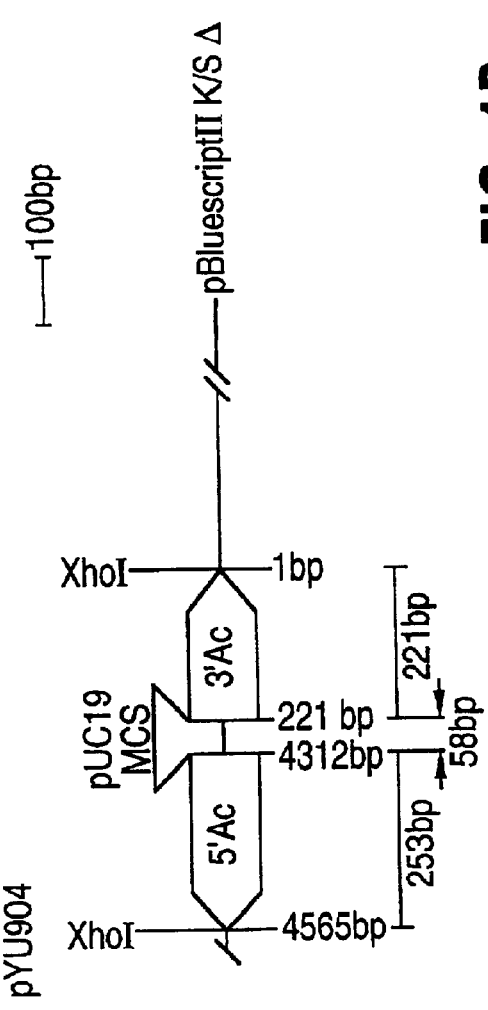
FIGS. 4A and 4B show schematics of pYU904 and pYU905 constructs, respectively.

A deletion derivative (pYU903) of pBLUESCRIPT II K/S (Stratagene) was constructed by first digesting with Sac I and Sal I, filling in with Klenow and religated. The plasmid was then digested with Asp 718 and Apa I, filled in with Klenow and relegated. The derivate plasmid represents a deletion of the restriction sites of the KpnI-SacI polylinker but with an intact XhoI cloning site.

pYU902 was digested with XhoI (New England Biolabs), and the internal 571 bp fragment was cloned into the XhoI site of pYU903 giving rise to pYU904 (FIG. 4A). This plasmid contains the 5' and 3' ends of Ac, and multiple cloning site within the Ds element that are now unique for the plasmid. This Ds element is referred to as "Ds-polylinker".

pYU905—Ds Element Containing Selectable Marker Gene

A 1.1 kb Sma I fragment containing the bar gene from Streptomyces hygroscopicus (Genbank Accession X17220) (SEQ ID NO:6) is fused to a 0.6 kb CaMV 35S promoter fragment (Benfey and Chua, 1990) and 3' polyadenylation signal element (coordinates 514–813) (GenBank Accession V00090) (SEQ ID NO:7) to create the plasmid pYU117.

Figure 4B:
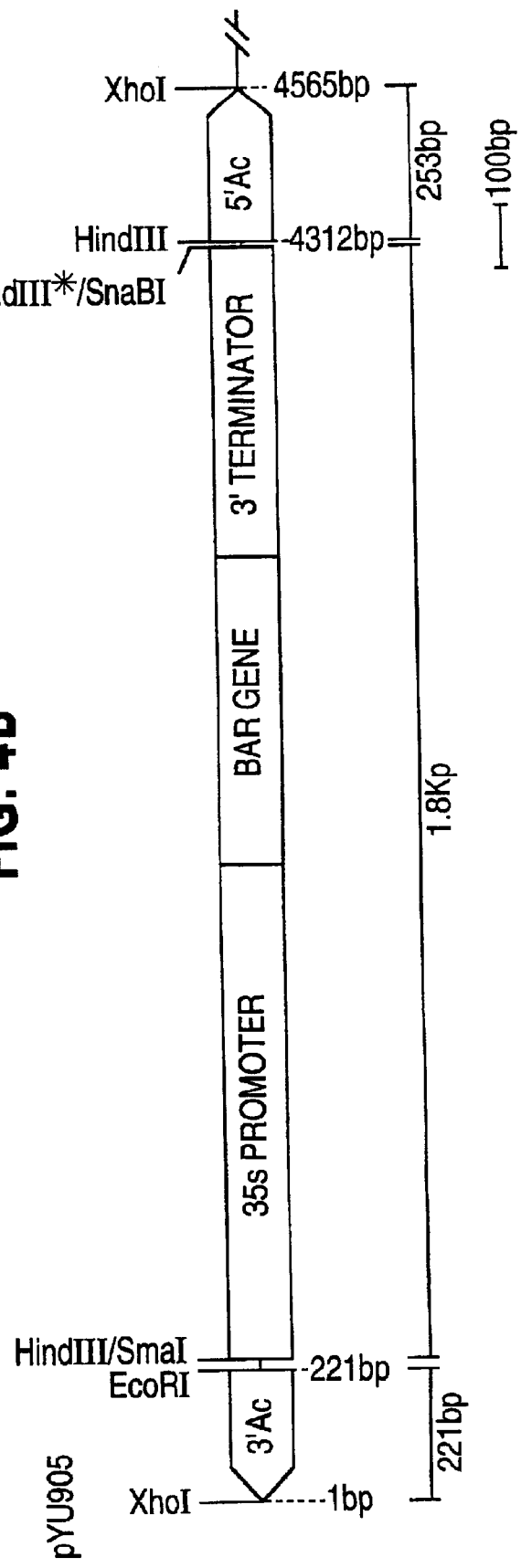

Plasmid pYU117 was digested with HindIII and SnaBI (new England Biolabs) and the 1.8 kb fragment containing the CaMV 35S promoter-bar gene-terminator gene was filled in with Klenow fragment DNA polymerase (New England Biolabs). The modified fragment was cloned into the SmaI site of pYU904 to generate pYU905 (FIG. 4B).

pYU905 contains the CaMV 35S-driven bar gene inside the Ds-polylinker transposable element. This synthetic Ds element is termed "Ds-bar".

pYU846—Transposase Source

Figure 5:
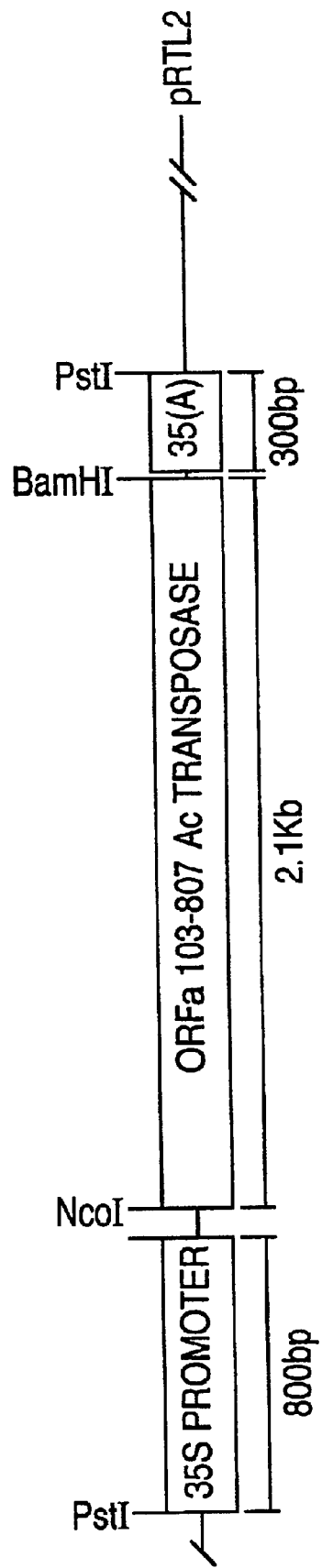
FIG. 5 shows a schematic of pYU846 transposase construct.

The plasmid pKU108A contains a transposase cDNA with a truncated reading frame (ORFa103-807) (Lee and Starlinger, PNAS 87:6044–6048. 1990) was digested with NcoI and BamHI (New England Biolabs). The internal 2.1 kb fragment was purified and subcloned into pRTL2 (Restrepo-Hartwig and Carrington. J. Virology 66:5662) previously digested with the same enzymes. The resulting plasmid, pYU846 (FIG. 5), contained a transcriptional fusion between the CaMV 35S promoter, the truncated Ac transposase cDNA (amino acidsl03-807) and the 35S polyadenylation sequence.

GST Constructs

Two examples of GST constructs based on the barnase gene of Bacillus amyloliquefaciens are shown in Table 1 (SEQ ID NO:15) and Table 2 (SEQ ID NO:16). These constructs are derived by replacing the tapetal-specific tobacco promoter TA29 (Genbank Accession A18052) (SEQ ID NO:8) with a dicot pollen-specific promoter from Arabidopsis thaliana (At59) or monocot pollen-specific promoter from Oryza sativa (rice) (GenBank Accession Z16402) (SEQ ID NO:9).

The At59 promoter and 5' UTR is amplified from A. thaliana Col-O genomic DNA using primers P755 (acccatgtgagttttctttcttctccat) (SEQ ID NO:10) and P756 (ttataggaaaattccagcagctcagcat) (SEQ ID NO:11). These primers simultaneously amplify the promoter and 5' UTR sequence while introducing a 5' Pst I cloning site and a 3' Nco I site situated at the start of translation. This Nco I site is fused to a 0.74 kb Nco I—Eco RI site of the barnase gene containing the nopaline synthase polyadenylation signal element at the 3' end to create the At59PSP:barnase:nos transgene (Table 1)(FIG. 3A).

Figure 3B:
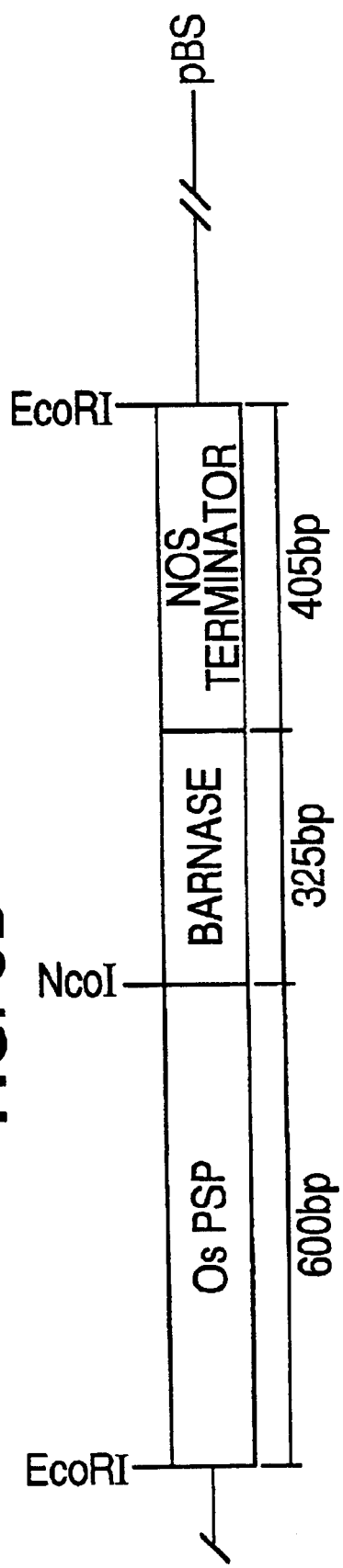

Likewise, the rice pollen-specific promoter (GenBank Accession Z16402) (SEQ ID NO:9) is amplified from Orza sativa ssp. indica IR36 genomic DNA using primers P731 (gaattccgggccatggcatcctttag) (SEQ ID NO:12) and P732 (ccatggatgatgtggctgcaaatg) (SEQ ID NO:13) which amplify a promoter and 5' UTR fragment while introducing a 5' EcoRI site and including the 3' Nco I site at the start of translation. This 0.74 kb Eco RI—Nco I fragment is ligated to the Nco I site of the barnase gene containing the nopaline synthase polyadenylation signal element at the 3' end to create the OsPSP:barnase:Nos transgene (Table 2)(FIG. 3B).

T-DNA Construct

The T-DNA vector pPZP200 (GenBank Accession U10460) (SEQ ID NO:14) is digested with Pst I ligated to the 3.2 kb Pst I fragment from pYU846 to generate pYU1001. pYU1001 is digested with Asp 718, filled in with Klenow, and ligated to the T4 DNA polymerase-treated 1.2 kb Pst I—Eco RI At59:barnase:nos gene fragment (pYU1002) or to the 1.3 kb Klenow-treated Eco RI OsPSP-:barnase:nos gene fragment (pYU1003).

pYU1002 or pYU1003 is digested with Sal I and ligated to the 2.3 kb Xho I Ds-bar element derived from pYU905 to give plasmid pYU1004 containing the GST, transposase source and Ds-bar element.

TABLE 1

Sequence and Features of AT59:Barnase:Nos GST Construct

| FEATURES | Location/Qualifiers |
|---|---|
| misc_feature | 840 . . 1245<br>/note = "3' regulatory sequence containing the polyadenylation site derived from the nopaline synthase gene from Agrobacterium T-DNA" |
| 5'UTR | 393 . . 503<br>AA changed to CC at 3' end to create NcoI site |
| TATA_signal | 364 . . 368 |
| primer_bind | 1 . . 30<br>change from CCAT to TGCA |
| primer_bind | complement (480 . . 501)<br>primer to amplify At59 promoter and introduce NcoI site |
| CDS | 504 . . 839<br>/note = "coding sequence of the barnase gene" |
| promoter | 1 . . 392 At59 promoter region |
| misc_feature | 1241 . . 1246 Eco RI cloning site |
| misc_feature | 1 . . 6 Pst I cloning site |

BASE COUNT
ORIGIN          400 a      232 c     235 g     375 t

```
   1  ctgcagggga ttttttaat tacttgtatg ataattattt tcaatagacc tagagacttg  (SEQ ID NO:15)
  61  atatatacta cgttaataa tcatatgtag tatgtatgat taattaagta aatacaaaaa
 121  tagttacctc aagttttaaa ggtgctattg ggtaattatc tcagtaaaaa taatattaga
 181  tcaaggcaaa aataactgaa aatatccaga aaagaaggat taaacaaagg catccaaaat
 241  ctataattgg gttttttgga gaaatgacca tagagattta aatcaatggt tgtctaatct
 301  atgttaattc tcaatcctct attgactctt ctcatctcct tttctctctc cccagttcct
 361  ggttattaaa gcaatcaggt gattcaaatc tttaatcttt taatcccggc aggcctatct
 421  gaaacaacaa cctccgtttg aggttttgcc gggaaaatat aaagttcaca ggctttggtc
 481  tctgcatttg caatatattt accatggtac cggttatcaa cacgtttgac ggggttgcgg
 541  attatcttca gacatatcat aagctacctg ataattacat tacaaaatca gaagcacaag
 601  ccctcggctg ggtggcatca aagggaacc ttgcagacgt cgctccgggg aaaagcatcg
 661  gcggagacat cttctcaaac agggaaggca aactcccggg caaaagcgga cgaacatggc
 721  gtgaagcgga tattaactat acatcaggct tcagaaattc agaccggatt ctttactcaa
 781  gcgactggct gatttacaaa acaacggacc attatcagac ctttacaaaa atcagataac
 841  gaaaaaaacg gcttcctgcg gaggccgttt ttttcagctt tacataaagt gtgtaataaa
 901  tttttcttca aactctgatc ggtcaatttc actttccggn nnnctctaga ggatccgaag
 961  cagatcgttc aaacatttgg caataaagtt tcttaagatt gaatcctgtt gccggtcttg
1021  cgatgattat catataattt ctgttgaatt acgttaagca tgtaataatt aacatgtaat
1081  gcatgacgtt atttatgaga tgggttttta tgattagagt cccgcaatta tacatttaat
1141  acgcgataga aaacaaaata tagcgcgcaa actaggataa attatcgcgc gcggtgtcat
1201  ctatgttact agatcgggaa gatccccggg taccgagctc gaattc
```

TABLE 2

Sequence and Features of OsPSP:Barnase: Nos GST Construct

| FEATURES | Location/Qualifiers |
|---|---|
| misc_feature | 1208 . . 1213<br>/note = "Eco RI cloning site" |
| misc_feature | 807 . . 1212<br>/note = "3' regulatory sequence containing the polyadenylation site derived from the nopaline synthase gene from Agrobacterium T-DNA" |
| CDS | 471 . . 806<br>/note = "coding sequence of the barnase gene" |
| misc_feature | 1 . . 6<br>/note = "Eco RI cloning site" |
| promoter | 6 . . 470<br>/note = "OsPSP promoter region" |

BASE COUNT
ORIGIN          374 a      279 c     239 g     317 t

```
   1  gaattccggg ccatggcatc ctttagaatg gaggaattta agtgaaattg agctaaacta  (SEQ ID NO:16)
  61  tgtgaacatc ctatgaagtt actgcattca aggcgcccaa catgaaatct attcaggttc
 121  ccaagttgtg ggcttccgta acgtcaaaat tcgacagatt tctggctggc taaaacaccc
 181  acaacggcaa taatagcctc gctcgtcaaa acattcaccc attttagct tggtcatcat
 241  caaaagtagg atcaaatcaa caatctgcct tctcttcagc cactcgatcc caacggcatc
 301  tccaacgatt cctacttgaa ggacagccat ggaaatcctc caggttcccc aggttactta
```

TABLE 2-continued

Sequence and Features of OsPSP:Barnase: Nos GST Construct

| | | | | | |
|---|---|---|---|---|---|
| 361 | taccacagct | cgaatccgtt | ccaaaccagg | ccatttcagt | accctcctct | cacattttcc |
| 421 | ccaaataata | atagaggaag | gggaaaaaca | catttgcagc | cacatcatcc | atggtaccgg |
| 481 | ttatcaacac | gtttgacggg | gttgcggatt | atcttcagac | atatcataag | ctacctgata |
| 541 | attacattac | aaaatcagaa | gcacaagccc | tcggctgggt | ggcatcaaaa | gggaaccttg |
| 601 | cagacgtcgc | tccggggaaa | agcatcggcg | gagacatctt | ctcaaacagg | gaaggcaaac |
| 661 | tcccgggcaa | aagcggacga | acatggcgtg | aagcggatat | taactataca | tcaggcttca |
| 721 | gaaattcaga | ccggattctt | tactcaagcg | actggctgat | ttacaaaaca | acggaccatt |
| 781 | atcagacctt | tacaaaaatc | agataacgaa | aaaaacggct | tcctgcggag | gccgtttttt |
| 841 | tcagctttac | ataaagtgtg | taataaattt | ttcttcaaac | tctgatcggt | caatttcact |
| 901 | ttccggnnnn | ctctagagga | tccgaagcag | atcgttcaaa | catttggcaa | taaagtttct |
| 961 | taagattgaa | tcctgttgcc | ggtcttgcga | tgattatcat | ataatttctg | ttgaattacg |
| 1021 | ttaagcatgt | aataattaac | atgtaatgca | tgacgttatt | tatgagatgg | gtttttatga |
| 1081 | ttagagtccc | gcaattatac | atttaatacg | cgatagaaaa | caaaatatag | cgcgcaaact |
| 1141 | aggataaatt | atcgcgcgcg | gtgtcatcta | tgttactaga | tcgggaagat | ccccgggtac |
| 1201 | cgagctcgaa | ttc | | | | |

Example 2

Preventing or Eliminating Transmission of a Transgene

When hemizygous, eliminating transmission of a transgene locus is achieved by linking a gene of interest to a suicide gene under the control of a male- or female-specific promoter. This construct, termed the "gametophytic suicide trait" (GST) induces cell death that is restricted to the microspores or megaspores which receive the GST, thereby effectively reducing or eliminating transmission of the gene of interest that is linked to the GST.

The gene carrying the special trait (i.e., transgene of interest) that you want to eliminate from transgenic pollen can be placed anywhere as long as it is in physical proximity to the GST. Because the GST transgene complex is hemizygous, there will be complete linkage in the GST transgene complex and there is no concern that the GST and other genes and/or transgenes will recombine.

The methods of this invention can be used with in planta or seed transformation techniques that do not require culture or regeneration. Examples of these techniques are described in Bechtold, N., et al. (1993) CR Acad. Sci. Paris/Life Sciences 316:1 118–93; Chang, S. S., et al. (1990) Abstracts of the Fourth International Conference on Arabidopsis Research, Vienna, p. 28; Feldmann, K. A. and Marks, D. M (1987) Mol. Gen. Genet. 208:1–9; Ledoux, L., et al. (1985) Arabidopsis Inf Serv. 22:1–11; Feldmann, K. A. (1992) In: Methods in Arabidopsis Research (Eds. Koncz, C., Chua, N -H, Schell, J.) pp. 274–289; Chee, et al., U.S. Pat. No. 5,376,543.

Arabidopsis.

Plasmids containing the GST constructs (i.e., AtS9PSP:barnase:nos or OsPSP:barnase:Nos) linked to the bar transgene are transformed by electroporation into Agrobacterium and then into Arabidopsis using the vacuum infiltration method (Bechtold et al., 1993, supra). As discussed previously, the bar gene construct codes for phosphinothricin acetyl transferase (PAT) driven by the CaMV 35S promoter to provide resistance to phophinothricin (PPT).

Transformants are selected based on resistance to PPT, and T2 seed is generated from a number of independent lines. This seed is plated on GM media containing various concentrations of herbicide and scored for germination and survival. Multiple transgenic lines overexpressing either the wild type or the resistant mutant produce significant numbers of green seedlings on an herbicide concentration that is lethal to the empty vector control.

The transgene or gene of interest to be included in the transgene complex and the initial transgenic lines need only be characterized for number of transgene loci and complexity of the transgene insertion in order to identify lines with single-copy, non-tandemly duplicated insertions. Characterization of the initial transgenics is accomplished by PCR and/or Southern analysis, both methods being well known to those skilled in the art of DNA amplification and gel electrophoresis.

Transformed plants hemizygous for the GST/transgene of interest, in this example the bar gene, are grown under the same growing conditions with transformed plants homozygous/heterozygous for the transgene of interest alone (i.e., no GST is present with the transgene) and with control, wild-type plants (i.e., plants lacking both GST and the transgene of interest) using appropriate statistical procedures (e.g., randomized complete block design or lattice design). Pollen is collected from the each of the individual plants and analyzed for the transgene and/or controlled crosses to wild-type plants are conducted and the seed is collected on a per plant basis and the resultant seeds/plants are analyzed for the transgene.

Plants hemizygous for the GST/transgene complex and wild-type plants produce pollen and/or seeds/plants all of which fail to contain the transgene of interest. In contrast, plants heterozygous for the transgene produce pollen and seeds/plants which show normal segregation for the transgene of interest. Plants homozygous for the transgene of interest produce pollen all of which contain the transgene of interest. Plants homozygous for the transgene of interest when crossed to wild-type plants produce F2 seeds/plants which show normal segregation patterns for the transgene of interest. Thus, plants hemizygous for the GST/transgene complex fail to produce pollen with the transgene while plants homozygous or heterozygous for the transgene alone produce at least some pollen which does contain the transgene of interest.

This is the same situation for the dispersed transposition aspect of the invention. The initial transgene complex carries both the GST and transposon and/or transposase. After the transgenic lines are generated, they are selected for dispersed transpositions. That is, one or two transgenic lines are all that are needed for subsequent selections. No further transformation is necessary. An additional, optional transgene, such as the CaMV 35S promoter/bar gene construct can be added if desired to aid in the selection of transformants.

Turfgrass

A nucleic acid construct (GST) in which the gene encoding barnase under the control of a pollen-specific promoter from maize is made such that the Roundup® resistance gene is linked to the GST. A virgin (i.e., wild-type) turfgrass genome is transformed with the transgene complex containing the three elements (maize pollen-specific promoter, barnase gene, Roundup® resistance gene) such that the resultant transgenic plant is hemizygous for the transgene complex.

The transgenic plant is vegetatively propagated to yield progeny plants that are also hemizygous for the transgene complex. Although all plants generated asexually from the transgenic plants are resistant to Roundup® treatment, transmission of the Roundup® resistance gene via cross-pollination is eliminated because no viable transgenic pollen is produced.

Since the GST construct is male-specific, the hemizygotic transgenic lines can be maintained by crossing to wild-type pollen. When transgene elimination is required (e.g., in selection for dispersed transpositions) then the hemizygotic transgenic lines are used as males (pollen donors) and crossed to wild-type females. In this instance, only non-transgenic pollen or pollen containing dispersed transpositions would be propagated. For the purposes of eliminating unwanted pollen transmission of a transgene (e.g., herbicide resistance in turfgrass), the hemizygotic transgenic lines can be planted and only wild-type pollen will survive.

Alfalfa

A nucleic acid construct (GST) in which the gene encoding barnase, under the control of a pollen-specific promoter from rice, is made such that a Bt gene is linked to the GST. A virgin (i.e., wild-type) alfalfa genome is transformed with the transgene complex containing the three elements (rice pollen-specific promoter, barnase gene, Bt gene) such that the resultant transgenic plant is hemizygous for the transgene complex.

The hemizygotic transgenic plant is vegetatively propagated to yield progeny plants that are also hemizygous for the transgene complex. Although the plant is resistant/tolerant to certain lepidopteran insect pests, transmission of the Bt gene via cross pollination is eliminated because no viable transgenic pollen is produced.

Transformed Corn

In the case of corn, the GST/transgene complex is inserted into the corn genome and the "female" parent carries the transgene complex. Upon hybridization with wild-type pollen, only ½ of the progeny hybrid seed will carry the transgene complex (not a problem for functional genomics applications). This limitation is circumvented by using a flp or lox recombinase system—the GST trait is kept inactive and homozygous until the hybrid is produced. At that point, frt—or cre-mediated recombination activates the GST trait (e.g., by removing a DNA block to transcription or by activating transcription), now present in all hybrid progeny instead of ½. The transgene complex containing activated GST is eliminated from any pollen inheriting the transgene complex (e.g. 50% of the meiotic products).

Example 3

Enriching Dispersed Transposition Events

By physically linking the sterility trait to a transposon launching site and/or transposase source, the "genetic sterility filter" is used to highly enrich for dispersed and/or stabilized transposition events without the use of chemicals and without the need to select against progeny containing linked transposition events and/or transposase source.

For instance, when 50% pollen sterility is achieved, the remaining viable haploid genomes will not have inherited the suicide gene and its associated elements such as the transposon launching site and/or transposase gene because of normal homologous chromosome segregation, independent assortment and meiotic recombination. A fraction of these viable genomes will contain newly transposed elements, especially those elements that have assorted independently or recombined from the launching site and its associated suicide gene. Therefore, the "genetic sterility filter" eliminates gametes containing transposed elements that remain linked to the launching site and/or gametes containing a transposase gene.

If the remaining viable pollen is used to fertilize ovules, either by controlled pollinations or by wind-pollination, a fraction of the resultant progeny will contain transposed elements. These progeny are readily identified by the inclusion of a selectable or screenable marker inside of the transposon, such as the petunia, Arabidopsis, or Agrobacterium CP4 EPSPS gene (Padgette, S. R. et al., (1987) Arch Biochem Biophys Vol. 258/2:564–73; Klee, H. J. et al., 1987 Mol Gen Genet Vol. 210/3:437–42; Hoef, A., et al., (1998) Food Addit Contam Vol.15/7:767–74; Harrison, L. A., et al, (1996) J Nutr Vol. 126/3:728–40), encoding glyphosate (Roundup®) resistance (Malik, J., et al., (1989) Biofactors Vol. 2/1:17–25); or a variety of acetolactate synthase (ALS) genes, encoding resistance to sulfonylurea herbicides (Whitcomb, C. E. (1999) Toxicol Ind Health Vol. 15/1–2:231–9), such as the Arabidopsis multiherbicide-resistant gene, csr1-4 (Mourad, G. et al., (1994) Mol Gen Genet Vol.: 243/2:178–84), or the bar gene from Streptomyces (Thompson, C. J et al., (1986) EMBO J. Vol. 6:2519–2523), encoding resistance to phosphinothricin (Finale®), to name a few.

In the case of the transmission of an autonomous element, such as Ac, progeny containing dispersed transposed Ac elements are identified by classical genetic means such as transactivation of a Ds-induced reporter gene. In one embodiment of the instant invention, the transposon is constructed with a pollen survival gene that permits only viable pollen that contain transposed elements, thereby completely eliminating the need for chemical selection or screens.

If the GST complex additionally contains a transposable element, then the frequency of transposition (both to linked and unlinked sites) can be high, depending on the source of transposase and other factors. Assuming a transposition frequency of 5%, 70% of which may be linked, then 30% are unlinked and 15% of these (random independent assortment of the transposon with the GST chromosome) will be recovered in progeny and easily identified by herbicide resistance contained on the transposable element. If we want to recover 100,000 independent insertions, an estimate of the number of seed required would be: $(100,000 \times 2/0.3)/0.05 = 13,333,333$ F1 seed needed. These could be generated and screened (recovered as individual plants) in less than 3 years.

Example 4

Enriching Stably Dispersed Transposition Events

A further embodiment of the instant invention is directed to inclusion, in the transgene complex, in addition to the transposon launching site and the suicide gene, other genes such as a transposase source. In this embodiment, the "genetic sterility filter" enriches for dispersed elements while also eliminating the transmission of the transposase source to progeny.

The simultaneous elimination of the transposon donor site and transposase gene has the added benefit of transmitting transposed elements that are stabilized (i.e. no longer transposing due to loss of the transposase gene) thereby preventing additional transpositions (secondary transpositions) from occurring.

Other embodiments of the instant invention include positioning the transposase source and transposon launching sites in separate transgene complexes. For instance, the launching site and the transposase source can be brought together in one genome on separate elements to achieve the same enrichment for dispersed transpositions. Moreover, in cases where localized transposition is desirable, i.e., to saturate a specific chromosomal region with insertions or to recover insertions in nearby genes of interest, the transposase source is eliminated by the sterility filter method without necessarily eliminating linked transpositions.

Example 5

Rice—A Model Plant System

A. Rice Transformation

Rice transgenics are generated employing a 24-well microtiter-based method that permits high throughput transgenic production. The method is an adaptation of published protocols (Hiei, Y., et al., (1994) Plant J. 6:271–82; Hiei, Y. et al. (1997) Plant Molec Bio. 35:205–218; Zhang, J., et al., (1997) Mol Biotechnol. 8:223–31) and involves an entirely liquid culturing and transformation system that allows the production of transgenic from scutellar callus induction, co-cultivation with Agrobacterium, treatment with Timentin, and shoot regeneration. This system is used to generate ca. 50–100 independent transgenic lines each month.

A tissue sample from each transgenic line is collected, DNA extracted and analyzed by Southern to identify lines that contain single copy T-DNA inserts (SCTLs). Shoots from SCTLs are micropropagated, rooted and transplanted to soil according to methods well known to one skilled in the art.

B. Genetic Methodologies

A broad-based, high volume-crossing program is available at CIAT for the generation of stocks, seed and transposon lines. Typically, about 1000 controlled (hand) crosses are made each cycle, including single, doubled, top and backcrosses. Number of F1 seeds obtained depends on the cross type and breeding objectives.

Crosses can be made throughout the year under biosafety-approved screenhouse conditions. Three plantings of parents at intervals of from 7 to 10 days are made to assure simultaneous flowering. Parents are grown in large pots or grown in the field in a hybridization block when employing the male-sterile female line.

For hand pollinations, the methods for crossing are: selection of parent plants, emasculation of panicles (removal of anthers for the female parent), covering of emasculated florets with a glassine bag, pollination of female parent with pollen collected from the male parent, covering of the pollinated panicle with the glassine bag, and identification of panicles used for crossing with a crossing tag containing relevant information about the parents, dates, and name of the person who did the crossing. For detailed information on the hybridization of rice see, for example, Coffman, W. R. and R. M. Herrera (1980) Rice, In: Hybridization of Crop Plants, W. R. Fehr and H. H. Hadley, Editors, Chapter 36: 511–522, American Society of Agronomists.

Selected F1 and T1 plants are harvested individually to produce F2 seeds. About 25 days after pollination hybrid seed is harvested, threshed, cleaned, placed in coin envelopes. This seed is stored under low humidity and temperature. T1 seed are grown in flats and selected for herbicide resistance by two foliar applications of 0.05% Finale® at 25 and 35 days after germination.

C. Sample Tracking

A relational, barcode sample tracking database can be used to track plants, seed, and DNA samples through the workflow. Each transgenic that is created is assigned a unique (alphanumeric) identifier. Stock plants derived from transgenics carry this identifier and a second unique stock identifier. All stocks that enter the production nurseries carry the transgenic/stock identifiers and testcross seed derived from each stock are assigned a unique identifier for each cross (T1 seed lot).

After Finale® selection, each resistant plant is assigned a unique line identifier. This information is coded on a plant label with two tearoff labels; each one contains identical alphanumerical identifiers and associated barcode. One tearoff label is attached to tissue sample and the other remains on the plant, ultimately stapled to the seed package. A widget bar code reader logs tissue samples into a database that then tracks samples through the DNA extraction queue and ultimately into a position of a 384-microtiter plate used for PCR amplification and DNA sequencing.

D. High-Throughput DNA Isolation and Normalization

Tissue samples are lyophilized prior to DNA extraction. Lyophilized tissue for shipping in plastic bags is sealed with desiccant. Tissue is ground with zirconium silica beads (ATGC, Inc.) by rapidly shaking 96–384 tubes on a commercial 10 gal paint shaker (Fluid Dynamics, Inc.).

The DNA is extracted using a high throughput, parallel method adapted from previously published methods (Galbiati, M., et al., (2000) Functional & Integrative Genomics, in press) and the purified DNA is stored in 96-format microtiter plate. DNA concentration is measured robotically by the Picogreen method (Molecular Probes, Inc.) using a Spectrofluor plate reader and Genesis robotics workstation (Tecan, Inc.).

To make a second working plate for PCR analysis, DNA is normalized robotically by removing a fixed amount of DNA from each well together with the appropriate amount of buffer into a second microtiter plate. Mother-daughter replicas of these normalized working plates are made robotically and samples are shipped for amplification and sequencing.

The feasibility of this entire procedure, including scripts, from tissue extraction to normalization, has been enabled for both maize and Arabidopsis.

E. Selection of Transposon Lines

Selection of transposon lines involves transgenic production and genetic testing for the recovery of single copy lines (SCLs), scaleup, sample tracking, processing and shipping followed by a production phase. Methods including DNA fingerprinting of T-DNA both in Agrobacterium inoculants and in primary rice transgenics, Agrobacterium-mediated transformation protocols, and methods for rice regeneration, micropropagation, and transplantation to soil may be employed.

Tissue is collected from each transgenic line, DNA extracted and analyzed by Southern analysis to identify single copy T-DNA lines (SCLs). All SCLs may be maintained in shoot culture and shipped for micropropagation. Rooted plantlets may be transplanted to soil and tested for transposition rates.

F. Stock Production

Genetic data on transposition frequencies is used to select for the best transgenic lines for continual stock production. Rooted shoots are transplanted to soil and further propagated by simple division to increase the numbers of male plants in the production nursery.

In one embodiment, if transpositions are limited to stamen development, an alternative, but not mutually exclusive method of stock propagation, is to cross wild-type pollen to the female transgenic plants—T-DNA elimination and transposition will not occur in this direction. Therefore, this seed can simply be replanted each season to generate additional stock for new transposition selections.

The flowering time for the rice variety Nipponbare is 60 days when grown at or near the equator. By using an equatorial location it is possible to achieve nearly 4 plant generations each year. The abbreviated generation time and constant year-round growing conditions in Cali, Mexico make rice genetics nearly as efficient as Arabidopsis.

G. Foundation Seed Production

In one embodiment of the instant invention, the objective is to select for single, dispersed transpositions and to recover these insertions in hemizygous condition. This permits the recovery of non-lethal, recessive lethal and female haplo-insufficient mutations.

To produce T1 seed, stock plants are crossed as males to male-sterile female plants in the nursery. Efficient outcrossing in rice can be achieved by interplanting males and male-sterile females. Male-sterility in Nipponbare is not presently available so a nuclear male sterility (ms) mutation is introgressed from an *O. sativa* ssp. *indica* strain into Nipponbare in the nurseries. The introgression process is greatly accelerated by marker-assisted mapping and breeding, selecting backcross progeny for the ms mutation and Nipponbare markers.

The ms locus is first mapped using previously characterized simple sequence repeat (SSR) markers (McCouch, S. R., et al., (1997) Plant Mol Biol. 35:89–99; Panaud, O., et al., (1996) Mol Gen Genet. 252:597–607). 7000 SSR sequences are available from the Monsanto rough draft (www.rice-research.org). Linked SSRs are used to follow the ms allele during introgression, while unlinked SSRs throughout the genome are used to select against donor germplasm.

Two backcrosses and one self pollination should be sufficient to transfer the ms allele to the Nipponbare background. The F1 crosses are made and F2 progeny are generated. The introgressed ms line is made available for T1 seed production. A 1:1 line segregating for the ms phenotype is used in the nursery, genotyped by SSR analysis, and the male-fertile plants culled. Transposon stocks are hybridized to ms/ms female plants to generate T1 seed for Ds line selection.

H. Transposon Line Selection

T1 seed is planted in flats and 25-day-old seedlings are selected by a foliar application of 0.05% Finale® followed by a second treatment 10–15 days later. Finale®-resistant plants are bar-coded and transplanted to the nursery and allowed to self-pollinate to generate T2 seed.

A tissue sample (ca. 1–2 gm leaf tissue) from each plant is collected, placed in bar-coded tubes, lyophilized and prepared for DNA extraction.

T2 seed from each line are collected, threshed, placed in bar-coded envelopes and prepared for storage or public distribution.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of eliminating transmission of a transgene of interest contained within the genome of a plant, wherein the method eliminates the production of pollen containing the transgene of interest by said plant and thereby prevents transmission of the transgene of interest by pollination with another plant, said method comprising:

a) producing a transformed plant that is hemizygotic but not homozygotic or heterozygotic for a nucleic acid construct comprising a pollen-specific promoter operably linked to a suicide coding region in close physical proximity to a transgene of interest;

b) growing the plant in step a) wherein said plant only produces pollen lacking said transgene of interest; and c) allowing the pollen from the plant grown in step b) to pollinate the same or another plant of the same species;

wherein said pollen does not contain the transgene of interest and transmission of said transgene of interest to said other plant is eliminated.

2. The method of claim 1, wherein said transformed plant produces about 50% less pollen compared to a wild-type non-transformed plant of the same species.

3. The method of claim 1, wherein the construct further comprises a promoter operably linked to a marker suitable for selection of the transformed plants.

4. The method of claim 1, wherein said pollination is cross-pollination.

5. The method of claim 1, wherein said nucleic acid construct comprising a pollen-specific promoter operably linked to a suicide coding region in close physical proximity to a transgene of interest is stably integrated into the genome of said transformed plant.

6. The method of claim 5, wherein said nucleic acid construct comprising the pollen-specific promoter operably linked to the suicide coding region which is in close physical proximity to the transgene of interest, are all maintained in close physical proximity to each other within the genome of the plant after being stably integrated into the genome of said plant.

7. A method of plant pollination that eliminates transmission of a transgene of interest contained within the genome of a plant, wherein the method eliminates the production of pollen containing the transgene of interest by said plant and thereby prevents transmission of the transgene of interest by cross-pollination, said method comprising:
  a) producing a transformed plant that is hemizygotic but not homozygotic or heterozygotic for a nucleic acid construct comprising a pollen-specific promoter operably linked to a suicide coding region in close physical proximity to a transgene of interest;
  b) growing the plant in step a) wherein said plant only produces pollen lacking said transgene of interest; and
  c) allowing the pollen from the plant grown in step b) to cross-pollinate a second plant of the same species;
wherein said pollen does not contain said transgene of interest and transmission of said transgene of interest to said second plant is eliminated.

* * * * *

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: 5' PCR primer

<400> SEQUENCE: 1
aagctttggc catattgcag tcatcc                26

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: 5' PCR primer

<400> SEQUENCE: 2

-continued

```
aagcttgctc gagcagggat gaaagtagga tggga                           35
```

<210> SEQ ID NO 3
<211> LENGTH: 4565
<212> TYPE: DNA
<213> ORGANISM: Zea mays
<220> FEATURE:
<223> OTHER INFORMATION: Transposable element Ac

<400> SEQUENCE: 3

```
tagggatgaa acggtcggt  aacggtcggt aaaatacctc taccgttttc attttcatat    60
ttaacttgcg gacggaaac  gaaaacggga tataccggta acgaaaacga acgggataaa   120
tacggtaatc gaaaaccgat acgatccggt cgggttaaag tcgaaatcgg acgggaaccg   180
gtatttttgt tcggtaaaat cacacatgaa acatatatt  caaaacttaa aaacaaatat   240
aaaaaattgt aaacacaagt cttaattaaa catagataaa atccatataa atctggagca   300
cacatagttt aatgtagcac ataagtgata agtcttgggc tcttggctaa cataagaagc   360
catataagtc tactagcaca catgacacaa tataaagttt aaaacacata ttcataatca   420
cttgctcaca tctggatcac ttagcatgca taaactatta caaccaaggc tcatctgtca   480
acaaacataa gacacattgc tcatggagag gagccacttg ctacatcttc attattctta   540
gaaaattcta ttgcgtcttc atcctgttaa tacacaaaaa taagtcagtt ttggataaat   600
aaatacatat agaagaacat gaattgatat gcagggagta taaataaata catataggag   660
aacatgaatc tgtgaactaa cacggctggg agctaggcag ctagcagcta gcgcctaaca   720
gctgggagcc taacagctag cagctagcag ccaatcaaaa caaggcgaca aggcgcatgc   780
agtgagatca aaaatctgtt aatgccagcc atgcaggag  tataacacgg ctgggcagca   840
aggcgcatgc atcaaaacaa ggcgacagca acagcccat  gcatcaaaac agtagtgaat   900
aatagcaaat taatagccca tgcacgaagt aaataataat ctttaaatac ctcatccata   960
tgattctcat gatttgttgc agcagcaata acagagtcta gcacctcgag atcaccaatc  1020
attgttggaa aatatgtagc accttgaatg acacaaatat gcatcaatat aagtaaaata  1080
attgttgaat aactataaat tggaacttca ttataacata tatgcattca cctttttctag 1140
atgctgctac ccaatctttt gtgcatatca aagcttcaac aatctccgaa ccaagacgat  1200
tgcggtaagg atcaacaaca cgaccaccag cactgaacgc agactcagaa gcaacagttg  1260
acacttgtat tgctagcaca tcccttgcaa tttgggtgag aataggatat tctgcaaccc  1320
ttcccctcca ccatgataaa atatcaaact gaccactatg cttcaaaagg ggttcagaca  1380
tatatttatc caattcattt gactctactt gatcataatc cttcaactca tgcaaatagt  1440
tttgaaattc atcatcttca ttttccatca aggtatcatc catactatca ttagtagttg  1500
tctttgtctt tggagctgaa ggactacaac tagaatagaa ttgatacaat tttctaatga  1560
ccctaacaaa gtcatctaca tgaactttgt atgaatcacc atgaaattt  tcatataga   1620
actcaatcaa tattttcttg tacctagggt caaggaagca tgctacagct agtgcaatat  1680
tagacacttt ccaatatttc tcaaactttt cactcattgc aacggccatt ctcctaatga  1740
caaattttc  atgaacacac cattggtcaa tcaaatcctt tatctcacag aaacctttgt  1800
aaaataaatt tgcagtggaa tattgagtac cagataggag ttcagtgaga tcaaaaaact  1860
tcttcaaaca cttaaaaaga gttaatgcca tcttccactc ctcggcttta ggacaaattg  1920
catcgtacct acaataattg acatttgatt aattgagaat ttataatgat gacatgtaca  1980
```

```
acaattgaga caaacatacc tgcgaggatc acttgtttta agccttatta gtgcaggctt    2040
ataatataag gcatccctca acatcaaata ggttgaattc catctagttg agacatcata    2100
tgagatccct ttagatttat ccaagtcaca ttcactagca cacttcatta gttcttccca    2160
ctgcaaagga gaagatttta cagcaagaac aatcgctttg attttctcaa ttgttcctgc    2220
aattacagcc aagccatcct ttgcaaccaa gttcagtatg tgacaagcac acctcacatg    2280
aaagaaagca ccatcacaaa ctagatttga atcagtgtcc tgcaaatcct caattatatc    2340
gtgcacagct acttcatttg cactagcatt atccaaagac aaggcaaaca attttttctc    2400
aatgttccac ttaaccatga ttgcagtgaa ggtttgtgat aacctttggc cagtgtggcg    2460
cccttcaaca tgaaaaaagc caacaattct tttttggaga caccaatcat catcaatcca    2520
atggatggtg acacacatgt atgacttatt ttgacaagat gtccacatat ccatagttgt    2580
actgaagcga gactgaacat cttttagttt tccatacaac ttttcttttt cttccaaata    2640
caaatccatg atatattttc tagcagtgac acgggacttt attggaaagt gagggcgcag    2700
agacttaaca aactcaacaa agtactcatg ttctacaata ttgaaaggat attcatgcat    2760
gattattgcc aaatgaagct tctttaggct aaccacttca tcgtacttat aaggctcaat    2820
gagatttatg tctttgccat gatccttttc acttttttaga cacaactgac ctttaactaa    2880
actatgtgat gttctcaagt gatttcgaaa tccgcttgtt ccatgatgac cctcagccct    2940
atacttagcc ttgcaattag gaaagttgca atgtccccat acctgaacgt atttctttcc    3000
atcgacctcc acttcaattt ccttcttggt gaaatgctgc catacatccg atgtgcactt    3060
ctttgccctc ttctgtggtg cttcttcttc gggttcaggt tgtggctgtg gttgtggttc    3120
tggttgtggt tgtggttgtg gttgtggttc atgaacaata gccatatcat cttgactcgg    3180
atctgtagct gtaccatttg cattactact gcttacactc tgaataaaat gcctctcggc    3240
ctcagctgtt gatgatgatg gtgatgtgcg gccacatcca tgcccacgcg cacgtgcacg    3300
tacattctga atccgactag aagaggcttc agcttttctt ttcaaccctg ttataaacag    3360
attttttcgta ttattctaca gtcaatatga tgcttcccaa tctacaacca attagtaatg    3420
ctaatgctat tgctactgtt tttctaatat ataccttgag catatgcaga gaatacggaa    3480
tttgttttgc gagtagaagg cgctcttgtg gtagacatca acttggccaa tcttatggct    3540
gagcctgagg gaggattatt tccaaccgga ggcgtcatct gaggaatgga gtcgtagccg    3600
gctagccgaa gtggagagca gagccctgga cagcaggtgt tcagcaatca gcttggtgct    3660
gtactgctgt gacttgtgag cacctggacg gctggacagc aatcagcagg tgttgcagag    3720
cccctggaca gcacacaaat gacacaacag cttggtgcaa tggtgctgac gtgctgtact    3780
gctaagtgct gtgagcctgt gagcagccgt ggagacaggg agaccgcgga tggccggatg    3840
ggcgagcgcc gagcagtgga ggtctggagg accgctgacc gcagatggcg gatgcggat    3900
gggcggaccg cggatgggcg agcagtggag tggaggtctg ggcggatggg cggaccgcgg    3960
cgcggatggg cgagtcgcga gcagtggagt ggagggcgga ccgtgatggg cggcgtctgc    4020
gtccggcgtg ccgcgtcacg gccgtcaccg cgtgtggtgc ctggtgcagc ccagcggccg    4080
gccggctggg agacagggag agtcggagag agcaggcgag agcgagacgc gtcgccggcg    4140
tcggcgtgcg gctggcggcg tccggactcc ggcgtgggcg cgtggcggcg tgtgaatgtg    4200
tgatgctgtt actcgtgtgg tgcctggccg cctgggagag aggcagagca gcgttcgcta    4260
ggtatttctt acatgggctg ggcctcagtg gttatggatg ggagttggag ctggccatat    4320
tgcagtcatc ccgaattaga aaatacggta acgaaacggg atcatcccga ttaaaaacgg    4380
```

```
gatcccggtg aaacggtcgg gaaactagct ctaccgtttc cgtttccgtt taccgttttg    4440
tatatcccgt ttccgttccg ttttcgtttt ttacctcggg ttcgaaatcg atcgggataa    4500
aactaacaaa atcggttata cgataacggt cggtacggga ttttcccatc ctactttcat    4560
ccctg                                                                4565

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:  3' PCR
      primer

<400> SEQUENCE: 4
gaattccctc gagtagggat gaaaacggtc ggtaac                                36

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:  3' PCR
      primer

<400> SEQUENCE: 5
gaattcgaat atatgttttc atgtgtgat                                        29

<210> SEQ ID NO 6
<211> LENGTH: 615
<212> TYPE: DNA
<213> ORGANISM: Streptomyces hygroscopicus
<220> FEATURE:
<223> OTHER INFORMATION: bar gene for phosphinothricin acetyl
      transferase

<400> SEQUENCE: 6
gaattcgagc tcggtacccg gggatctacc atgagcccag aacgacgccc ggccgacatc      60
cgccgtgcca ccgaggcgga catgccggcg gtctgcacca tcgtcaacca ctacatcgag     120
acaagcacgg tcaacttccg taccgagccg caggaaccgc aggagtggac ggacgacctc     180
gtccgtctgc gggagcgcta tccctggctc gtcgccgagg tggacggcga ggtcgccggc     240
atcgcctacg cgggccccctg gaaggcacgc aacgcctacg actggacggc cgagtcgacc     300
gtgtacgtct ccccccgcca ccagcggacg ggactgggct ccacgctcta cacccacctg     360
ctgaagtccc tggaggcaca gggcttcaag agcgtggtcg ctgtcatcgg gctgcccaac     420
gacccgagcg tgcgcatgca cgaggcgctc ggatatgccc ccgcggcat gctgcgggcg     480 gccggcttca gcacgggaa ctggcatgac gtgggtttct ggcagctgga cttcagcctg     540
ccggtaccgc ccgtccggt cctgcccgtc accgagatct gatgacccgg gggatccctg     600
caggcatgca agctt                                                     615

<210> SEQ ID NO 7
<211> LENGTH: 831
<212> TYPE: DNA
<213> ORGANISM: Agrobacterium tumefaciens
<220> FEATURE:
<221> NAME/KEY: polyA_signal
<222> LOCATION: (514)..(813)

<400> SEQUENCE: 7
```

```
cgagcattttt atggattttc ttcagatgag actagttcaa gcttgaaaat taagcccccc    60 cccccgaaatc atcgccagag gtcgtcccag cccggcatct atatatagcg ccaatatagt   120
ttgtcttaca caaacacacc tcacatcatg aatttcgcag atactccctt ggcctccctc   180
gacctagact gggcatgcga agagtttatc aaaacttatg gtgcatctcc acaattggaa   240
acaggagagg taatccaaac aaacaatggg ctgctgtatt tgtatggcaa aggttcactc   300
tcacagcgga ttcatgacac acacctcaaa tttaaggaga aggaagaatt atccttcact   360
accataaagc cagctgagat gaaggcgcaa caaagtgatt taacttatta tgtcgccatt   420
tttcaaagca actatttcct gtgcgtttca aatccagaga aaggctttct gagatgccat   480
aatcgcccat ttctgtaccc catagtagcc catggatcga tgagctaagc tagctatatc   540
atcaatttat gtattacaca taatatcgca ctcagtcttt catctacggc aatgtaccag   600
ctgatataat cagttattga aatatttctg aatttaaact tgcatcaata aatttatgtt   660
tttgcttgga ctataatacc tgacttgtta ttttatcaat aaatatttaa actatatttc   720
tttcaagata tcattcttta caagtatacg tgtttaaatt gaataccata aatttttatt   780
tttcaaatac atgtaaaatt atgaaatggg agtggtggcg accgagctca a             831

<210> SEQ ID NO 8
<211> LENGTH: 1287
<212> TYPE: DNA
<213> ORGANISM: Artificial Sequence
<220> FEATURE:
<223> OTHER INFORMATION: Description of Artificial Sequence:  Construct-
      TA29:barnase:A. tumefaciens poly-A site
<221> NAME/KEY: unsure
<222> LOCATION: (982)..(985)
<223> OTHER INFORMATION: n = a or c or g or t.

<400> SEQUENCE: 8
atctagctaa gtataactgg ataatttgca ttaacagatt gaatatagtg ccaaacaaga    60
agggacaatt gacttgtcac tttatgaaag atgattcaaa catgattttt tatgtactaa   120
tatatacatc ctactcgaat taaagcgaca taggctcgaa gtatgcacat ttagcaatgt   180
aaattaaatc agttttttgaa tcaagctaaa agcagacttg cataaggtgg gtggctggac   240
tagaataaac atcttctcta gcacagcttc ataatgtaat ttccataact gaaatcaggg   300
tgagacaaaa ttttggtact ttttcctcac actaagtcca tgtttgcaac aaattaatac   360
atgaaacctt aatgttaccc tcagattagc ctgctactcc ccatttttcct cgaaatgctc   420 caacaaaagt tagttttgca agttgttgtg tatgtcttgt gctctatata tgcccttgtg   480
gtgcaagtgt aacagtacaa catcatcact caaatcaaag tttttactta agaaaattag   540
ctaccatggt accggttatc aacacgtttg acggggttgc ggattatctt cagacatatc   600
ataagctacc tgataattac attacaaaat cagaagcaca agccctcggc tgggtggcat   660
caaaagggaa ccttgcagac gtcgctccgg ggaaaagcat cggcggagac atcttctcaa   720
acagggaagg caaactcccg ggcaaaagcg gacgaacatg gcgtgaagcg gatattaact   780
atacatcagg cttcagaaat tcagaccgga ttctttactc aagcgactgg ctgatttaca   840
aaacaacgga ccattatcag acctttacaa aaatcagata acgaaaaaaa cggcttcctg   900
cggaggccgt ttttttcagc tttacataaa gtgtgtaata aattttttctt caaactctga   960 tcggtcaatt tcactttccg gnnnnctcta gaggatccga agcagatcgt tcaaacattt  1020
ggcaataaag tttcttaaga ttgaatcctg ttgccggtct tgcgatgatt atcatataat  1080
ttctgttgaa ttacgttaag catgtaataa ttaacatgta atgcatgacg ttatttatga  1140
```

```
gatggtttt tatgattaga gtcccgcaat tatacattta atacgcgata gaaaacaaaa      1200
tatagcgcgc aaactaggat aaattatcgc gcgcggtgtc atctatgtta ctagatcggg      1260
aagatccccg ggtaccgagc tcgaatt                                         1287
```

<210> SEQ ID NO 9
<211> LENGTH: 1303
<212> TYPE: DNA
<213> ORGANISM: Oryza sativa
<220> FEATURE:
<223> OTHER INFORMATION: Pollen-specific gene

<400> SEQUENCE: 9

```
ccgggccatg gcatccttta gaatggagga atttaagtga aattgagcta aactatgtga       60
acatcctatg aagttactgc attcaaggcg cccaacatga aatctattca ggttcccaag      120
ttgtgggctt ccgtaacgtc aaaattcgac agatttctgg ctggctaaaa cacccacaac      180
ggcaataata gcctcgctcg tcaaaacatt cacccatttt tagcttggtc atcatcaaaa      240
gtaggatcaa atcaacaatc tgccttctct tcagccactc gatcccaacg gcatctccaa      300
cgattcctac ttgaaggaca gccatggaaa tcctccaggt tccccaggtt acttatacca      360
cagctcgaat ccgttccaaa ccaggccatt tcagtaccct cctctcacat tttccccaaa      420
taataataga ggaaggggaa aaacacattt gcagccacat catccatggc ctctctccgc      480
accattccgg tgatcttcgg catcctcttc tatgtccttg ccagcactgc cactgccacc      540
gacgcaccag actacgtcgt ccaaggccgt gtctactgtg acacgtgccg cgccgagttc      600
gagaccaatg tcaccgagta tatcaagggt aaggaaattc ttttttgggt caggagtctg      660
caatgaaaat gctgaaatga ataacctccg atatatgagc agcagaactt aggaagacca      720
aagaactgca gagtttgtgc atcaatttgt aaacatgaaa cgctaacctg gttagaagtc      780
cagcattggc tcacctgatc tcttgattgc aggtgccaag gtcaggctgg agtgcaagca      840
ctttggcacc gacaaggtcg agcgtgcgat tgacggtgtg actgatgaga ccgggacata      900
caagattgag ctcaaggaca gccatgagga ggacatctgc gaggttgtcc tcgtccacag      960 ccccccttgca aactgctctg aaatcgaggc cgaaagggat cgtgcccgtg ttttgctcac     1020
caggaatgtc ggcatctgtg acaacctgcg cttagccaac ccactcggct acctcaagga     1080
ctaccactgc ccgtctgcgg cgctgctcaa gcagttcgac ctggctgatg atgataacga     1140
gtaatgcgat gatcgtcatg gaacctccgg agaggctgca ttaattataa atcagttaga     1200
ggcttgcaaa atagcatgga tctatctgaa aggcagaact aagcatatgt caaaacatga     1260
aatgtacact catcactaag tactcacatg tgactacctg agg                       1303
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 10

```
acccatgtga gtttctttct tctccat                                           27
```

<210> SEQ ID NO 11
<211> LENGTH: 28
<212> TYPE: DNA
<213> ORGANISM: Artificial Sequence

```
<220> FEATURE:
<223> OTHER INFORMATION: Description of Artificial Sequence: 5' PCR
      primer

<400> SEQUENCE: 11
ttataggaaa attccagcag ctcagcat                                          28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 12
gaattccggg ccatggcatc ctttag                                            26

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: 5' PCR
      primer

<400> SEQUENCE: 13
ccatggatga tgtggctgca aatg                                              24

<210> SEQ ID NO 14
<211> LENGTH: 6741
<212> TYPE: DNA
<213> ORGANISM: Artificial Sequence
<220> FEATURE:
<223> OTHER INFORMATION: Description of Artificial Sequence: Cloning
      vector pPZP200 for plant transformation

<400> SEQUENCE: 14
agtactttga tccaacccct ccgctgctat agtgcagtcg gcttctgacg ttcagtgcag       60
ccgtcttctg aaaacgacat gtcgcacaag tcctaagtta cgcgacaggc tgccgccctg      120 ccctttttcct ggcgttttct tgtcgcgtgt tttagtcgca taaagtagaa tacttgcgac     180
tagaaccgga gacattacgc catgaacaag agcgccgccg ctggcctgct gggctatgcc     240
cgcgtcagca ccgacgacca ggacttgacc aaccaacggg ccgaactgca cgcggccggc     300
tgcaccaagc tgttttccga aagatcacc ggcaccaggc gcgaccgccc ggagctggcc      360
aggatgcttg accacctacg ccctggcgac gttgtgacag tgaccaggct agaccgcctg     420
gcccgcagca cccgcgacct actggacatt gccgagcgca tccaggaggc cggcgcgggc     480
ctgcgtagcc tggcagagcc gtgggccgac accaccacgc cggccggccg catggtgttg     540
accgtgttcg ccggcattgc cgagttcgag cgttccctaa tcatcgaccg cacccggagc     600
gggcgcgagg ccgccaaggc ccgaggcgtg aagtttggcc ccgccctac cctcacccccg    660 gcacagatcg cgcacgcccg cgagctgatc gaccaggaag gccgcaccgt gaaagaggcg     720
gctgcactgc ttggcgtgca tcgctcgacc ctgtaccgcg cacttgagcg cagcgaggaa     780
gtgacgccca ccgaggccag gcggcgcggt gccttccgtg aggacgcatt gaccgaggcc     840
gacgccctgg cggccgccga gaatgaacgc caagaggaac aagcatgaaa ccgcaccagg     900
acggccagga cgaaccgttt ttcattaccg aagagatcga ggcggagatg atcgcggccg    960
ggtacgtgtt cgagccgccc gcgcacgtct caaccgtgcg gctgcatgaa atcctggccg    1020
```

```
gtttgtctga tgccaagctg gcggcctggc cggccagctt ggccgctgaa gaaaccgagc    1080
gccgccgtct aaaaaggtga tgtgtatttg agtaaaacag cttgcgtcat gcggtcgctg    1140
cgtatatgat gcgatgagta aataaacaaa tacgcaaggg gaacgcatga aggttatcgc    1200
tgtacttaac cagaaaggcg ggtcaggcaa gacgaccatc gcaacccatc tagcccgcgc    1260
cctgcaactc gccggggccg atgttctgtt agtcgattcc gatccccagg gcagtgcccg    1320
cgattgggcg gccgtgcggg aagatcaacc gctaaccgtt gtcggcatcg accgcccgac    1380
gattgaccgc gacgtgaagg ccatcggccg gcgcgacttc gtagtgatcg acggagcgcc    1440
ccaggcggcg gacttggctg tgtccgcgat caaggcagcc gacttcgtgc tgattccggt    1500
gcagccaagc ccttacgaca tatgggccac cgccgacctg gtggagctgg ttaagcagcg    1560
cattgaggtc acggatggaa ggctacaagc ggcctttgtc gtgtcgcggg cgatcaaagg    1620
cacgcgcatc ggcggtgagg ttgccgaggc gctggccggg tacgagctgc ccattcttga    1680
gtcccgtatc acgcagcgcg tgagctaccc aggcactgcc gccgccggca caaccgttct    1740
tgaatcagaa cccgagggcg acgctgcccg cgaggtccag gcgctggccg ctgaaattaa    1800
atcaaaactc atttgagtta atgaggtaaa gagaaaatga gcaaaagcac aaacacgcta    1860
agtgccggcc gtccgagcgc acgcagcagc aaggctgcaa cgttggccag cctggcagac    1920
acgccagcca tgaagcgggt caactttcag ttgccggcgg aggatcacac caagctgaag    1980
atgtacgcgg tacgccaagg caagaccatt accgagctgc tatctgaata catcgcgcag    2040
ctaccagagt aaatgagcaa atgaataaat gagtagatga attttagcgg ctaaaggagg    2100
cggcatggaa aatcaagaac aaccaggcac cgacgccgtg gaatgcccca tgtgtggagg    2160
aacgggcggt tggccaggcg taagcggctg ggttgtctgc cggccctgca atggcactgg    2220
aacccccaag cccgaggaat cggcgtgacg gtcgcaaacc atccggcccg gtacaaatcg    2280
gcgcggcgct gggtgatgac ctggtggaga agttgaaggc cgcgcaggcc gcccagcggc    2340
aacgcatcga ggcagaagca cgccccggtg aatcgtggca agcggccgct gatcgaatcc    2400
gcaaagaatc ccggcaaccg ccggcagccg gtgcgccgtc gattaggaag ccgcccaagg    2460
gcgacgagca accagatttt ttcgttccga tgctctatga cgtgggcacc cgcgatagtc    2520
gcagcatcat ggacgtggcc gttttccgtc tgtcgaagcg tgaccgacga gctggcgagg    2580
tgatccgcta cgagcttcca gacgggcacg tagaggtttc cgcagggccg gccggcatgg    2640
ccagtgtgtg ggattacgac ctggtactga tggcggtttc ccatctaacc gaatccatga    2700
accgataccg ggaagggaag ggagacaagc ccggccgcgt gttccgtcca cacgttgcgg    2760
acgtactcaa gttctgccgg cgagccgatg gcggaaagca gaaagacgac ctggtagaaa    2820
cctgcattcg gttaaacacc acgcacgttg ccatgcagcg tacgaagaag gccaagaacg    2880
gccgcctggt gacggtatcc gagggtgaag ccttgattag ccgctacaag atcgtaaaga    2940
gcgaaaccgg gcggccggag tacatcgaga tcgagctagc tgattggatg taccgcgaga    3000
tcacagaagg caagaacccg gacgtgctga cggttcaccc cgattacttt ttgatcgatc    3060
ccggcatcgg ccgttttctc taccgcctgg cacgccgcgc cgcaggcaag gcagaagcca    3120
gatggttgtt caagacgatc tacgaacgca gtggcagcgc cggagagttc aagaagttct    3180
gtttcaccgt gcgcaagctg atcgggtcaa atgacctgcc ggagtacgat ttgaaggagg    3240
aggcggggca ggctggcccg atcctagtca tgcgctaccg caacctgatc gagggcgaag    3300
catccgccgg ttcctaatgt acggagcaga tgctagggca aattgcccta gcaggggaaa    3360
aaggtcgaaa aggtctcttt cctgtggata gcacgtacat tgggaaccca agccgtaca    3420
```

```
ttgggaaccg gaacccgtac attgggaacc caaagccgta cattgggaac cggtcacaca   3480
tgtaagtgac tgatataaaa gagaaaaaag gcgatttttc cgcctaaaac tctttaaaac   3540
ttattaaaac tcttaaaacc cgcctggcct gtgcataact gtctggccag cgcacagccg   3600
aagagctgca aaaagcgcct acccttcggt cgctgcgctc cctacgcccc gccgcttcgc   3660
gtcggcctat cgcggccgct ggccgctcaa aaatggctgg cctacggcca ggcaatctac   3720
cagggcgcgg acaagccgcg ccgtcgccac tcgaccgccg cgcccacat caaggcaccc    3780 tgcctcgcgc gtttcggtga tgacggtgaa aacctctgac acatgcagct cccggagacg   3840
gtcacagctt gtctgtaagc ggatgccggg agcagacaag cccgtcaggg cgcgtcagcg   3900
ggtgttggcg ggtgtcgggg cgcagccatg acccagtcac gtagcgatag cggagtgtat   3960
actggcttaa ctatgcggca tcagagcaga ttgtactgag agtgcaccat atgcggtgtg   4020
aaataccgca cagatgcgta aggagaaaat accgcatcag gcgctcttcc gcttcctcgc   4080
tcactgactc gctgcgctcg gtcgttcggc tgcggcgagc ggtatcagct cactcaaagg   4140
cggtaatacg gttatccaca gaatcagggg ataacgcagg aaagaacatg tgagcaaaag   4200
gccagcaaaa ggccaggaac cgtaaaaagg ccgcgttgct ggcgtttttc cataggctcc   4260
gcccccctga cgagcatcac aaaaatcgac gctcaagtca gaggtggcga acccgacag    4320 gactataaag ataccaggcg tttccccctg gaagctccct cgtgcgctct cctgttccga   4380
ccctgccgct taccggatac ctgtccgcct ttctcccttc gggaagcgtg gcgctttctc   4440
atagctcacg ctgtaggtat ctcagttcgg tgtaggtcgt tcgctccaag ctgggctgtg   4500
tgcacgaacc ccccgttcag cccgaccgct gcgccttatc cggtaactat cgtcttgagt   4560
ccaacccggt aagacacgac ttatcgccac tggcagcagc cactggtaac aggattagca   4620
gagcgaggta tgtaggcggt gctacagagt tcttgaagtg gtggcctaac tacggctaca   4680
ctagaaggac agtatttggt atctgcgctc tgctgaagcc agttaccttc ggaaaaagag   4740
ttggtagctc ttgatccggc aaacaaacca ccgctggtag cggtggtttt tttgtttgca   4800
agcagcagat tacgcgcaga aaaaaggat ctcaagaaga tcctttgatc ttttctacgg   4860
ggtctgacgc tcagtggaac gaaaactcac gttaagggat tttggtcatg catgatatat   4920
ctcccaattt gtgtagggct tattatgcac gcttaaaaat aataaaagca gacttgacct   4980
gatagtttgg ctgtgagcaa ttatgtgctt agtgcatcta atcgcttgag ttaacgccgg   5040
cgaagcggcg tcggcttgaa cgaatttcta gctagacatt atttgccgac taccttggtg   5100
atctcgcctt tcacgtagtg gacaaattct tccaactgat ctgcgcgcga ggccaagcga   5160
tcttcttctt gtccaagata agcctgtcta gcttcaagta tgacgggctg atactgggcc   5220
ggcaggcgct ccattgccca gtcggcagcg acatccttcg gcgcgatttt gccggttact   5280
gcgctgtacc aaatgcggga caacgtaagc actacatttc gctcatcgcc agcccagtcg   5340
ggcggcgagt tccatagcgt taaggtttca tttagcgcct caaatagatc ctgttcagga   5400
accggatcaa agagttcctc cgccgctgga cctaccaagg caacgctatg ttctcttgct   5460
tttgtcagca agatagccag atcaatgtcg atcgtggctg gctcgaagat acctgcaaga   5520
atgtcattgc gctgccattc tccaaattgc agttcgcgct tagctggata acgccacgga   5580
atgatgtcgt cgtgcacaac aatggtgact tctacagcgc ggagaatctc gctctctcca   5640
ggggaagccg aagtttccaa aagtcgttg atcaaagctc gccgcgttgt tcatcaagc    5700 cttacggtca ccgtaaccag caaatcaata tcactgtgtg gcttcaggcc gccatccact   5760
```

-continued

```
gcggagccgt acaaatgtac ggccagcaac gtcggttcga gatggcgctc gatgacgcca    5820
actacctctg atagttgagt cgatacttcg gcgatcaccg cttcccccat gatgtttaac    5880
tttgttttag ggcgactgcc ctgctgcgta acatcgttgc tgctccataa catcaaacat    5940
cgacccacgg cgtaacgcgc ttgctgcttg gatgcccgag gcatagactg taccccaaaa    6000
aaacatgtca taacaagaag ccatgaaaac cgccactgcg ccgttaccac cgctgcgttc    6060
ggtcaaggtt ctggaccagt tgcgtgacgg cagttacgct acttgcatta cagcttacga    6120
accgaacgag gcttatgtcc actgggttcg tgcccgaatt gatcacaggc agcaacgctc    6180
tgtcatcgtt acaatcaaca tgctaccctc cgcgagatca tccgtgtttc aaacccggca    6240
gcttagttgc cgttcttccg aatagcatcg gtaacatgag caaagtctgc cgccttacaa    6300
cggctctccc gctgacgccg tcccggactg atgggctgcc tgtatcgagt ggtgattttg    6360
tgccgagctg ccggtcgggg agctgttggc tggctggtgg caggatatat tgtggtgtaa    6420
acaaattgac gcttagacaa cttaataaca cattgcggac gttttaatg tactgaatta     6480 acgccgaatt gaattcgagc tcggtacccg gggatcctct agagtcgacc tgcaggcatg    6540
caagcttagc ttgagcttgg atcagattgt cgtttcccgc cttcagttta aactatcagt    6600
gtttgacagg atatattggc gggtaaacct aagagaaaag agcgtttatt agaataacgg    6660
atatttaaaa gggcgtgaaa aggtttatcc gttcgtccat ttgtatgtgc atgccaacca    6720
cagggttccc ctcgggatca a                                              6741
```

<210> SEQ ID NO 15
<211> LENGTH: 1246
<212> TYPE: DNA
<213> ORGANISM: Artificial Sequence
<220> FEATURE:
<223> OTHER INFORMATION: Description of Artificial Sequence: Construct-
      AT59:Barnase:Nos GST
<221> NAME/KEY: unsure
<222> LOCATION: (940)..(943)
<223> OTHER INFORMATION: n = a or c or g or t.

<400> SEQUENCE: 15

```
ctgcagggga ttttttttaat tacttgtatg ataattattt tcaatagacc tagagacttg     60
atatatacta cgtttaataa tcatatgtag tatgtatgat taattaagta aatacaaaaa    120
tagttacctc aagttttaaa ggtgctattg ggtaattatc tcagtaaaaa taatattaga    180
tcaaggcaaa ataactgaa aatatccaga aaagaaggat taaacaaagg catccaaaat    240
ctataattgg gttttttgga gaaatgacca tagagattta aatcaatggt tgtctaatct    300
atgttaattc tcaatcctct attgactctt ctcatctcct tttctctctc ccagttcct     360 ggttattaaa gcaatcaggt gattcaaatc tttaatcttt taatcccggc aggcctatct    420
gaaacaacaa cctccgtttg aggttttgcc gggaaaatat aaagttcaca ggctttggtc    480
tctgcatttg caatatattt accatggtac cggttatcaa cacgtttgac ggggttgcgg    540
attatcttca gacatatcat aagctacctg ataattacat acaaaatcca gaagcacaag    600
ccctcggctg ggtggcatca aagggaacc ttgcagacgt cgctccgggg aaaagcatcg    660
gcggagacat cttctcaaac agggaaggca actcccggg caaaagcgga cgaacatggc    720
gtgaagcgga tattaactat acatcaggct tcagaaattc agaccggatt ctttactcaa    780
gcgactggct gatttacaaa acaacggacc attatcagac ctttacaaaa atcagataac    840
gaaaaaaacg gcttcctgcg gaggccgttt ttttcagctt tacataaagt gtgtaataaa    900
tttttcttca aactctgatc ggtcaatttc actttccggn nnnctctaga ggatccgaag    960
```

-continued

```
cagatcgttc aaacatttgg caataaagtt tcttaagatt gaatcctgtt gccggtcttg    1020
cgatgattat catataattt ctgttgaatt acgttaagca tgtaataatt aacatgtaat    1080
gcatgacgtt atttatgaga tgggttttta tgattagagt cccgcaatta tacatttaat    1140
acgcgataga aaacaaaata tagcgcgcaa actaggataa attatcgcgc gcggtgtcat    1200
ctatgttact agatcgggaa gatccccggg taccgagctc gaattc                  1246

<210> SEQ ID NO 16
<211> LENGTH: 1213
<212> TYPE: DNA
<213> ORGANISM: Artificial Sequence
<220> FEATURE:
<223> OTHER INFORMATION: Description of Artificial Sequence:  Construct-
      OsPSP:Barnase:Nos GST
<221> NAME/KEY: unsure
<222> LOCATION: (907)..(910)
<223> OTHER INFORMATION: n = a or c or g or t.

<400> SEQUENCE: 16
gaattccggg ccatggcatc ctttagaatg gaggaattta agtgaaattg agctaaacta      60
tgtgaacatc ctatgaagtt actgcattca aggcgcccaa catgaaatct attcaggttc     120
ccaagttgtg ggcttccgta acgtcaaaat tcgacagatt tctggctggc taaaacaccc     180
acaacggcaa taatagcctc gctcgtcaaa acattcaccc attttagct tggtcatcat      240 caaaagtagg atcaaatcaa caatctgcct tctcttcagc cactcgatcc caacggcatc     300
tccaacgatt cctacttgaa ggacagccat ggaaatcctc caggttcccc aggttactta     360
taccacagct cgaatccgtt ccaaaccagg ccatttcagt accctcctct cacattttcc     420
ccaaataata atagaggaag gggaaaaaca catttgcagc cacatcatcc atggtaccgg     480
ttatcaacac gtttgacggg gttgcggatt atcttcagac atatcataag ctacctgata    540
attacattac aaaatcagaa gcacaagccc tcggctgggt ggcatcaaaa gggaaccttg     600
cagacgtcgc tccggggaaa agcatcggcg gagacatctt ctcaaacagg gaaggcaaac     660
tcccgggcaa aagcggacga acatggcgtg aagcggatat taactataca tcaggcttca    720
gaaattcaga ccggattctt tactcaagcg actggctgat ttacaaaaca acggaccatt     780
atcagacctt tacaaaaatc agataacgaa aaaaacggct tcctgcggag gccgtttttt    840
tcagctttac ataagtgtg taataaattt ttcttcaaac tctgatcggt caatttcact     900
ttccggnnnn ctctagagga tccgaagcag atcgttcaaa catttggcaa taaagtttct    960
taagattgaa tcctgttgcc ggtcttgcga tgattatcat ataatttctg ttgaattacg   1020
ttaagcatgt aataattaac atgtaatgca tgacgttatt tatgagatgg gttttatga   1080 ttagagtccc gcaattatac atttaatacg cgatagaaaa caaatatag cgcgcaaact    1140 aggataaatt atcgcgcgcg gtgtcatcta tgttactaga tcgggaagat ccccgggtac   1200
cgagctcgaa ttc                                                       1213
```